United States Patent
Sweeney

(10) Patent No.: US 11,517,723 B2
(45) Date of Patent: Dec. 6, 2022

(54) MODULAR GUIDEWIRE

(71) Applicant: Spinal Generations, LLC

(72) Inventor: Patrick J. Sweeney, Flossmoor, IL (US)

(73) Assignee: Spinal Generations, LLC, Mokena, IL (US)

( * ) Notice: Subject to any disclaimer, the term of this patent is extended or adjusted under 35 U.S.C. 154(b) by 464 days.

(21) Appl. No.: 15/861,449

(22) Filed: Jan. 3, 2018

(65) Prior Publication Data

US 2018/0185618 A1    Jul. 5, 2018

Related U.S. Application Data

(60) Provisional application No. 62/442,258, filed on Jan. 4, 2017.

(51) Int. Cl.
*A61M 25/09* (2006.01)
*A61M 25/06* (2006.01)
*A61M 25/00* (2006.01)

(52) U.S. Cl.
CPC ........ *A61M 25/09* (2013.01); *A61M 25/0662* (2013.01); *A61M 25/0905* (2013.01); *A61M 25/0074* (2013.01); *A61M 2025/09108* (2013.01); *A61M 2025/09175* (2013.01); *A61M 2025/09183* (2013.01)

(58) Field of Classification Search
CPC .............. A61M 25/09; A61M 25/0662; A61M 25/0905; A61M 25/0074; A61M 25/09016; A61M 25/09025; A61M 25/0668; A61M 25/0071; A61M 2025/09108; A61M 2025/09175; A61M 2025/09183; A61M 2025/09091; A61M 2025/09058; A61M 2025/09116

See application file for complete search history.

(56) References Cited

U.S. PATENT DOCUMENTS 4,966,163 A * 10/1990 Kraus ............... A61M 25/0905
403/77
5,109,867 A    5/1992 Twyford, Jr.
5,271,415 A   12/1993 Foerster et al.
(Continued)

FOREIGN PATENT DOCUMENTS

WO     WO-92/18051 A1    10/1992

OTHER PUBLICATIONS

International Search Report and Written Opinion regarding International Application No. PCT/US2018/012233, dated Apr. 13, 2018, 14 pps.

(Continued)

*Primary Examiner* — Allen Porter
*Assistant Examiner* — Avery M Foley
(74) *Attorney, Agent, or Firm* — Foley & Lardner LLP

(57) ABSTRACT

A guidewire having a first end and a second end, and comprising two or more guidewire modules. Each guidewire module has a first end and a second end. Each guidewire module is configured to be attachable to a second guidewire module by at least one of: attaching the first end of the guidewire module with the second end of the second guidewire module, and attaching the second end of the guidewire module with the first end of the second guidewire module.

18 Claims, 13 Drawing Sheets

(56) References Cited

U.S. PATENT DOCUMENTS

| | | | |
|---|---|---|---|
| 2001/0016712 A1* | 8/2001 | Hamilton | A61M 25/0113 |
| | | | 604/170.01 |
| 2006/0074442 A1* | 4/2006 | Noriega | A61M 25/09 |
| | | | 606/159 |
| 2008/0051676 A1 | 2/2008 | Melsheimer | |
| 2008/0051721 A1 | 2/2008 | Carter et al. | |
| 2009/0082722 A1* | 3/2009 | Munger | A61M 25/0113 |
| | | | 604/95.01 |
| 2009/0187098 A1* | 7/2009 | Makower | A61B 5/411 |
| | | | 600/424 |
| 2010/0305475 A1 | 12/2010 | Hinchliffe et al. | |
| 2014/0358123 A1* | 12/2014 | Ueda | A61M 25/0097 |
| | | | 604/510 |
| 2015/0174379 A1* | 6/2015 | Bagaoisan | A61M 25/0075 |
| | | | 604/509 |

OTHER PUBLICATIONS

Foreign Action other than Search Report on PCT PCT/US2018/012233 dated Jul. 18, 2019, 7 pps.

\* cited by examiner

MODULAR GUIDEWIRE

CROSS-REFERENCE TO RELATED APPLICATIONS

The application claims the benefit of and priority to U.S. Provisional Application No. 62/442,258, filed on Jan. 4, 2017, which is hereby incorporated by reference in its entirety.

BACKGROUND

The present invention relates generally to the field of surgical tools and implements, and more particularly to guidewires for use in surgical and related healthcare settings.

Guidewires are used in many surgical procedures carried out in a healthcare setting. For example, in orthopedic trauma surgery, guidewires are often used to connect two fragments of a bone fracture. The guidewire allows for guided tool and implant insertion into the bone through the sliding of cannulated tools and implants over the guidewire connecting the two bone fragments.

Guidewires are typically made of stainless steel and designed to be disposable, though some are designed of different materials and/or designed to be reusable. They may come equipped with one of a variety of tips, depending on the guidewire's purpose. Guidewires also come in various lengths and diameters, depending on where in a patient's skeletal anatomy the guidewire is to be used. Additionally, guidewires may be contoured in the operating room by surgical staff to suit a need of the a patient (e.g., to help a surgeon find a canal of a fragment of a fractured implant).

However, some procedures require longer guidewires which can range up to 100 cm (approximately 40 inches), making them awkward to transport. Moreover, maneuvering longer guidewires in small or cramped conditions can be difficult and threaten the sterility of the guidewire. As such, a guidewire with, e.g., customizable length and/or tip options would be desirable in many healthcare settings.

SUMMARY OF THE INVENTION

One embodiment of the invention relates to a guidewire having a first end and a second end, and comprised of two or more guidewire modules. Each guidewire module has a first end and a second end. Each guidewire module is configured to be attachable to a different guidewire module by at least one of the first end of the guidewire module with the second end of the different guidewire module, and the second end of the guidewire module with the first end of the different guidewire module.

Another embodiment of the invention relates to a modular guidewire supply kit comprising three or more guidewire modules, each guidewire module having a first end and a second end. Each guidewire module is configured to be attachable to a different guidewire module by at least one of the first end of the guidewire module with the second end of the second guidewire module, and the second end of the guidewire module with the first end of the different guidewire module. In this embodiment, a completed guidewire comprises at least two of the three or more guidewire modules attached together.

Another embodiment of the invention relates to a method for building a guidewire of customizable length. The method comprises determining a desired length for a guidewire, and selecting at least two guidewire modules from a set comprising at least three guidewire modules, each guidewire module having a first end and a second end. The method further comprises attaching the two or more guidewire modules together by connecting either the first end of each guidewire module with the second end of a different guidewire module, or the second end of the guidewire module with the first end of the different guidewire module. Furthermore, the method comprises attaching a guidewire tip to the first end or the second end of one of the attached two or more guidewire modules, the guidewire of customizable length comprising the attached two or more guidewire modules and the guidewire tip.

BRIEF DESCRIPTION OF THE DRAWINGS

FIG. 2b is an end view of an inserting endpiece of the guidewire module of FIG. 2a.

FIG. 2d is an end view of a receiving endpiece of the guidewire module of FIG. 2a.

FIG. 2f depicts two of the guidewire modules embodied in FIG. 2a.

FIG. 5b depicts an embodiment of a modular guidewire including one of the guidewire tips embodied in FIG. 5a.

FIG. 6b depicts an embodiment of a modular guidewire including one of the guidewire tips embodied in FIG. 6a.

FIG. 11b depicts an embodiment of a modular guidewire including the endcap guidewire modules embodied in FIG. 11a.

FIG. 12b depicts the modular guidewire embodied in FIG. 11a assembled including the guidewire sheath embodied in FIG. 12a.

DETAILED DESCRIPTION

Figure 1:
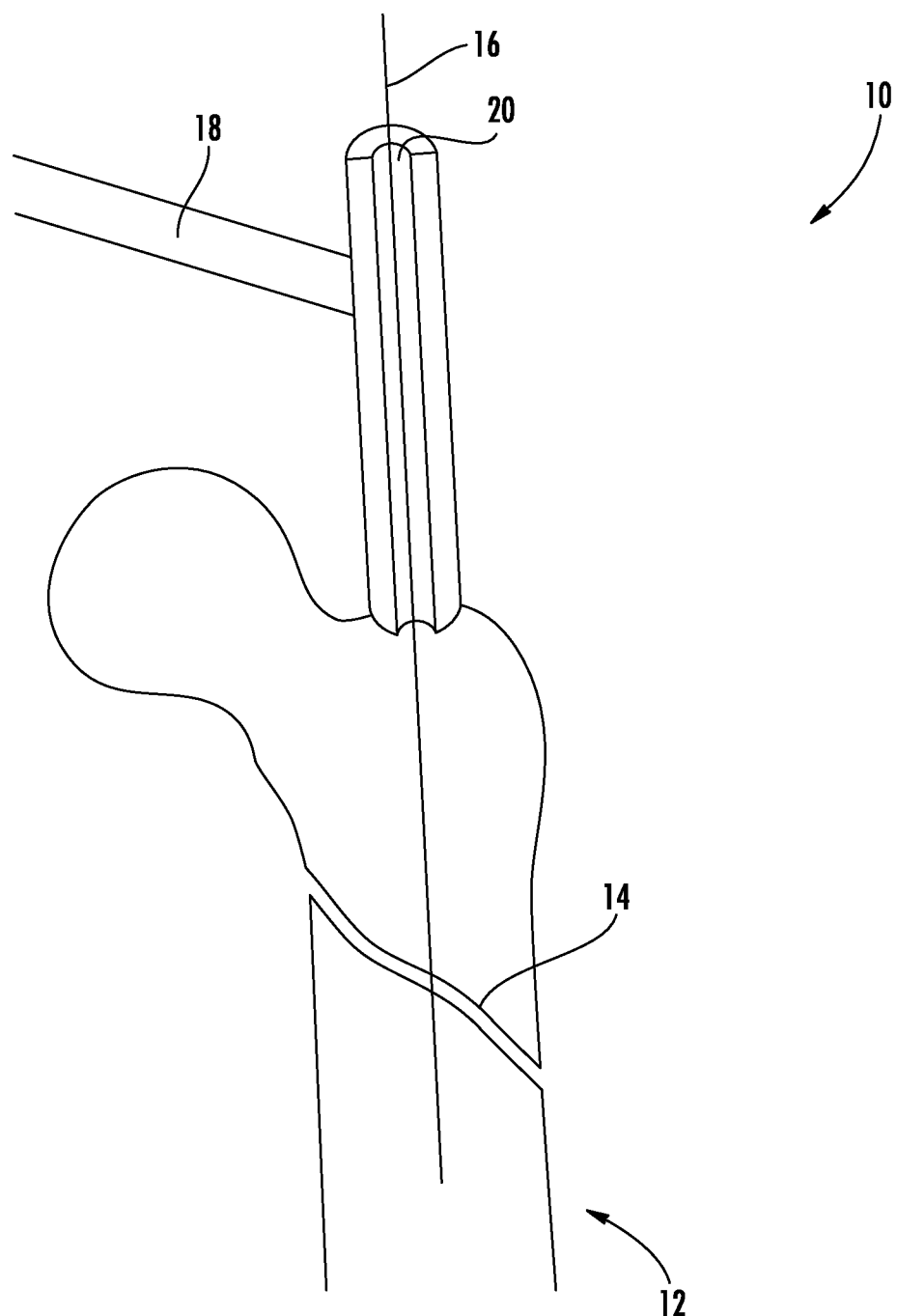
FIG. 1 is a cross-sectional view of a guidewire in use during an orthopedic trauma surgery.

Guidewires are designed to be used in a variety of surgical procedures in a healthcare setting. As an example of a surgical procedure using a guidewire, FIG. 1 illustrates a stage, labeled as step 10, of an orthopedic trauma surgery to repair a broken bone, shown as bone 12, of a patient. As shown in step 10 of FIG. 1, the bone 12 contains a fracture line 14 in need of repairing. As part of step 10 of the orthopedic trauma surgery, a guidewire 16 has been inserted down the shaft of the bone 12 and roughly orthogonal to the fracture line 14 by using a drill guide 18. The drill guide includes a cannula 20 configured to threadably slide over the guidewire 16. This threadable connection between the guidewire 16 and the drill guide 18 helps ensure the desired placement of the guidewire 16 in the bone 12. In later stages of the orthopedic trauma surgery, the guidewire 16 may also serve as a placement guide for additional orthopedic surgical instruments, such as a cannulated drill bit, a cannulated screwdriver, and/or a cannulated screw.

Figure 2A:
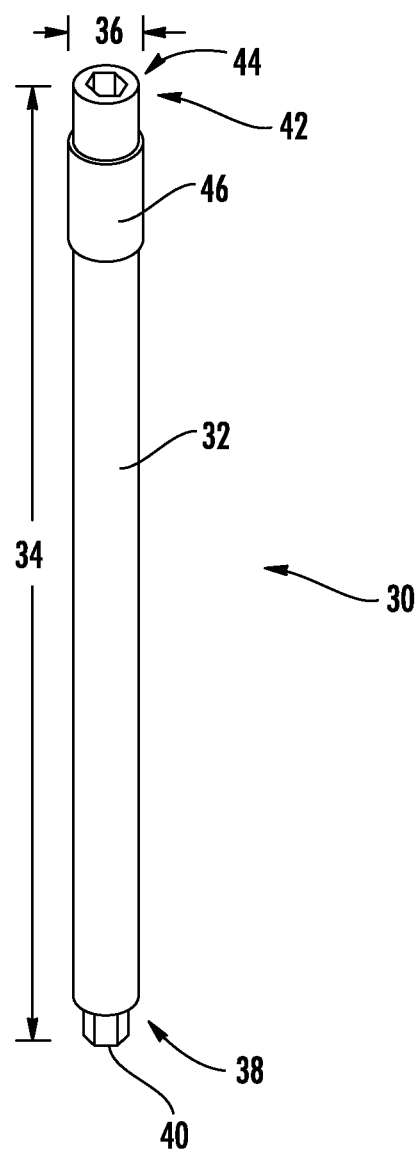
FIG. 2a is a side view of a guidewire module, in accordance with an exemplary embodiment.

Guidewires, such as the guidewire 16 of FIG. 1, are typically of pre-specified length and may also include a pre-specified guidewire tip. As such, guidewires typically lack customizability to, e.g., adapt to a particular surgical facility or to an anatomy of a patient. For at least these reasons, a guidewire comprised of a plurality of guidewire modules, allowing for customizability of the guidewire, may be desirable for steps of a surgical procedure, such as step 10 shown in FIG. 1. FIG. 2a illustrates an embodiment of a guidewire module 30. The guidewire module 30 may be configured to be disposable, intended for a single use, or reusable. The guidewire module 30 comprises a cylindrical body 32, where a length 34 of the body 32 is greater than a diameter 36 of the body 32. In some embodiments, the guidewire module 30 has a diameter between 1.0 mm and 3.2 mm. The body 32 of the guidewire module 30 includes a first connecting end 38 with an inserting endpiece 40, and a second connecting end 42 with a receiving endpiece 44. As shown in FIG. 2a, the inserting endpiece 40 and the receiving endpiece 44 are configured to be interlocking, such that, given a second guidewire module 30, the inserting endpiece 40 may be inserted into the connecting endpiece 44. As shown in FIG. 2a, the guidewire module 30 may also include a sleeve 46.

The body 32 of the guidewire module 30 may be made of a material common to guidewires, such as stainless steel, a high-tensile stainless steel, nitinol, a hybrid of stainless steel and nitinol, etc. A material of the body 32 may be machined to provide the guidewire module 30 with specific properties (e.g., be micro-cut with grooves to allow for enhanced precision and control). The body 32 of the guidewire module 30 may also be at least partially covered in a coating, such as a silicone-based coating, a PTFE (polytetrafluoroethylene) coating, a different polymer coating, a hydrophilic coating, a hydrophobic coating, etc.

Figure 2B:
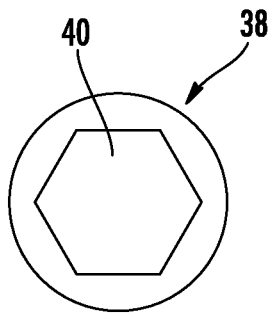
Figure 2C:
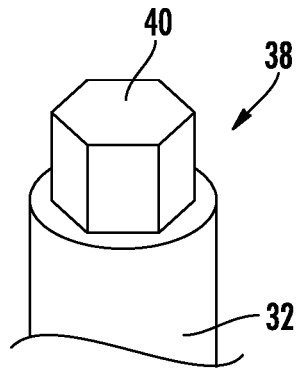
FIG. 2c is a perspective view of the inserting endpiece shown in FIG. 2b.
Figure 2D:
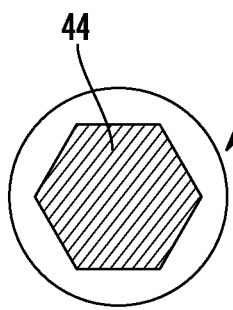
Figure 2E:
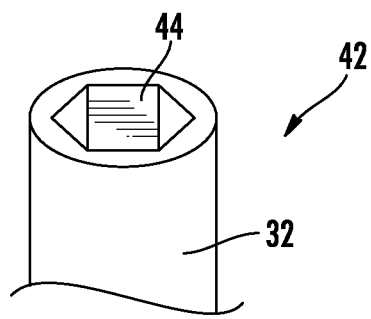
FIG. 2e is a perspective view of the receiving endpiece shown in FIG. 2d.

FIGS. 2b and 2c show a close-up view of the first connecting end 38 of the guidewire module 30, including the inserting endpiece 40. In the embodiment shown in FIGS. 2b and 2c, the inserting endpiece 40 is a hexagonal piece that extends from the body 32 of the guidewire module 30. FIGS. 2d and 2e show a close-up view of the second connecting end 42 of the guidewire module 30, including the receiving endpiece 44. In the embodiment shown in FIGS. 2d and 2e, the receiving endpiece 44 is a hexagonal-shaped recess in the body 32 of the guidewire module 30. However, those of ordinary skill in the art will appreciate that FIGS. 2b-2e are not intended to be limiting. Rather, FIGS. 2b-2e are intended to be illustrative of example embodiments of an inserting endpiece 40 and a receiving endpiece 44. This application also envisions other designs and configurations for the inserting endpiece 40 and the receiving endpiece 44.

Figure 2F:
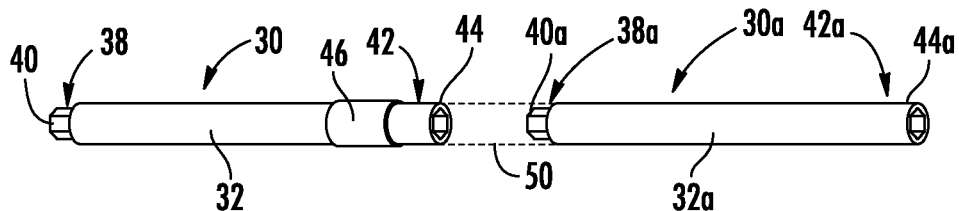

FIG. 2f shows the guidewire module 30, along with a second guidewire module 30a configured similarly to the guidewire module 30. The second guidewire module 30a also comprises a cylindrical body 32a, a first connecting end 38a with an inserting endpiece 40a, and a second connecting end 42a with a receiving endpiece 44a. Guidewire modules 30 and 30a may be of equal length or may have differing lengths. As shown in FIG. 2f, the inserting endpieces 40 and 40a are configured to be interlocking with the receiving endpieces 44 and 44a. As an example, the inserting endpiece 40 of the guidewire module 30 may be inserted into the receiving endpiece 44a of the second guidewire module 30a. As another example, the inserting endpiece 40a of the second guidewire module 30a may be inserted into the receiving endpiece 44 of the guidewire module 30. Dashed lines 50 illustrate an insertion path for this second example, i.e., where the inserting endpiece 40a of the second guidewire module 30a is inserted into the receiving endpiece 44 of the guidewire module 30. By connecting the interlocking endpieces 44 and 40a as shown in FIG. 2f, or the interlocking endpieces 40 and 44a as described, the guidewire module 30 and the second guidewire module 30a may be connected together.

Figure 2G:
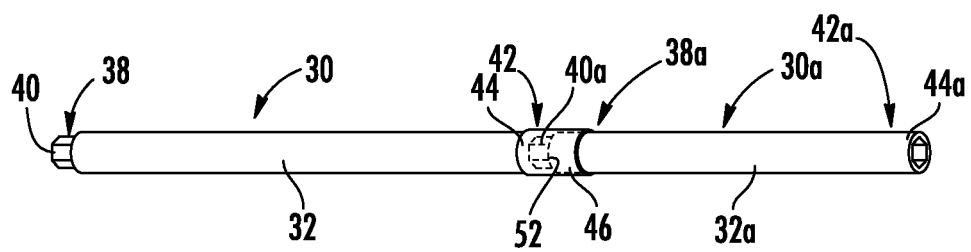
FIG. 2g depicts the two of the of the guidewire modules embodied in FIG. 2a, connected together.

FIG. 2g shows the guidewire module 30 and the second guidewire module 30a connected together as shown by the insertion path 50 of FIG. 2f, i.e., via an interlocking connection, shown as connection 52, between the receiving endpiece 44 of the guidewire module 30 and the inserting endpiece 40a of the second guidewire module 30a. The connection 52 between the inserting endpiece 40a and the receiving endpiece 44 attaches the guidewire module 30 to the second guidewire module 30a in such a way to limit rotation between the guidewire module 30 and the second guidewire module 30a (e.g., because of the shape of the inserting endpiece 40 and the receiving endpiece 44 which prevents rotation, because of friction between the inserting endpiece 40a and the receiving endpiece 44 and/or because ridges of the inserting endpiece 40a prevent the inserting endpiece 40a from slipping or rotating within the receiving endpiece 44).

In the embodiment of FIG. 2g, the sleeve 46 of guidewire module 30 has been threaded over the connection 52. The sleeve 46 further prevents rotation and separation between the guidewire module 30 and the second guidewire module 30a, essentially "locking" the connection 52 between the guidewire module 30 and the second guidewire module 30a in a rigid fashion. However, this application also envisions other configurations of guidewire modules 30 that do not include a sleeve 46 to prevent rotation and/or separation between the guidewire modules 30.

In the embodiment of a guidewire module shown in FIGS. 2a-2g, the endpiece at the first connecting end 38 (inserting endpiece 40) is a "male" endpiece, and the endpiece at the second connecting end 42 (receiving endpiece 44) is a "female" endpiece. However, those of ordinary skill in the art will appreciate that the endpiece at the first connecting end 38 may be a female endpiece and the endpiece at the second connecting end 42 may be a male endpiece, such that, given another guidewire module 30, the endpiece at the second connecting end 42 is configured to be inserted into the endpiece at the first connecting end 38. Moreover, those of ordinary skill in the art will appreciate that the first endpiece 40 and the second endpiece 44 may be designed in a variety of configurations allowing for a connection between a first and a second guidewire module 30. As an example, a version of the guidewire module 30 may include male endpieces at the first connecting end 38 and the second connecting end 42. In this example, a second version of the guidewire module 30 may include female endpieces at its first connecting end 38 and its second connecting end 42, such that the first version of the guidewire module 30 may connect to the second version of the guidewire module 30 by either of the connecting ends of each.

In the embodiment of FIGS. 2a-2g, the inserting endpieces 40 and 40a and the receiving endpieces 44 and 44a are designed to be removably interlocking, such that the guidewire module 30 and the second guidewire module 30a may be separated after being connected together. As an example, and referring to FIG. 2g, one could separate the guidewire module 30 from the second guidewire module 30a by threading the sleeve 46 back over the body 32 of the guidewire module 30 (e.g., to the position the sleeve 46 occupies on the body 32 in FIG. 2b) and gently pulling the guidewire module 30 away from the guidewire module 30a until they separate at the connection 52. The ability to disassemble connected guidewire modules 30 may be desirable to surgical staff because, e.g., it may allow the surgical staff to reuse the guidewire modules 30. However, this application also envisions embodiments of guidewire modules 30 that permanently attach, i.e., cannot be separated once the inserting endpiece 40 of one guidewire module 30 is connected to the receiving endpiece 44 of a second guidewire module 30. In such embodiments, the guidewire modules 30 would be disposable and intended for a single use.

Figure 3:
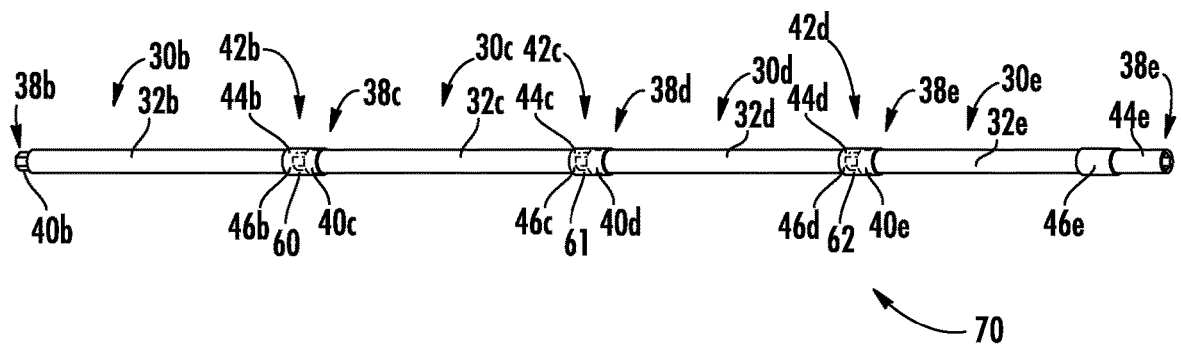
FIG. 3 depicts a plurality of the guidewire modules embodied in FIG. 2a, assembled into an embodiment of a modular guidewire.

FIG. 3 illustrates a plurality of the guidewire module 30, shown as guidewire modules 30b-30e. Similar to guidewire module 30 shown in FIGS. 2a-2g, guidewire modules 30b-30e comprise guidewire bodies 32b-32e, first connecting ends 38b-38e with inserting endpieces 40b-40e, second connecting ends 42b-42e with receiving endpieces 44b-44e, and sleeves 46b-46e. The guidewire modules 30b-30e are connected together as described above with respect to FIGS. 2a-2g such that they form a plurality of interlocking connections, shown as connections 60-62.

Together, the connected guidewire modules 30b-30e form a guidewire, shown as modular guidewire 70. The modular guidewire 70 can be used in stages of a surgical procedure, such as step 10 of the orthopedic trauma surgery shown in FIG. 1. However, unlike the guidewire 16 shown in FIG. 1, the modular guidewire 70 is customizable with respect to at least a length of the modular guidewire 70. As an example, the modular guidewire 70 may be lengthened by adding further guidewire modules 30 at the inserting endpiece 40b of guidewire module 30b and/or at the receiving endpiece 44e of guidewire module 30e, in a manner similar to that described above with respect to FIGS. 2a-2g. (As shown in FIG. 3, the guidewire module 30e includes an unused sleeve 46e to facilitate the "locking" attachment of an additional guidewire module 30 at the receiving end 38e of the guidewire module 30e.) As another example, the modular guidewire 70 may be shortened by removing one or more of the guidewire modules 30b-30e from the modular guidewire 70, in the manner similar to that described above with respect to FIGS. 2a-2g. Customization of the modular guidewire 70 may also occur by adding a differently sized guidewire module to one or both ends of the modular guidewire 70 (i.e., at the first connecting end 38b of the guidewire module 30b and/or at the second connecting end 38e of the guidewire module 30e), by adding one of a plurality of guidewire tips to one of the ends of the modular guidewire 70, by using a different version of sleeves 46b-46e to lock the connections 60-62 of the modular guidewire 70 into place, etc.

Customization of the modular guidewire 70 may occur prior to or during a surgical procedure, and may be based on an anatomy of a patient undergoing surgery, the needs of surgical staff performing the surgery, limitations of the environment the surgery is being conducted in, etc. As an example, surgical staff assemble the modular guidewire 70 from 15 guidewire modules 30 because of a modular guidewire 70 to reach a location of a bone fracture within a patient. As another example, the surgical staff may assemble the modular guidewire 70 from eight guidewire modules 30 because space in the operating room the surgery is being conducted in is limited and the surgical staff believe a shorter version of the modular guidewire 70 is less likely to lose its sterility in the limited operating space.

Additionally, because the modular guidewire 70 may be assembled in an operating room, the modular guidewire 70 may be transported to the operating room in a disassembled form, i.e., as the smaller, individual guidewire modules 30b-30e. The fact that the modular guidewire 70 may be transported in a disassembled form may make it easier to transport to and within a healthcare facility, particularly if the modular guidewire 70 is very long, than a non-modular guidewire of similar length. Moreover, if a surgical staff determine that one of the guidewire modules 30b-30e is fatigued or otherwise unsuitable for use, the surgical staff may replace the unsuitable guidewire module with a new guidewire module 30. This is advantageous to the surgical staff because the staff can keep the remainder of the modular guidewire 70, replacing just the unsuitable guidewire module. In contrast, with a non-modular guidewire, if the surgical staff determines that a portion of the non-modular guidewire is fatigued or otherwise unsuitable for use, the staff must replace the entire guidewire.

The guidewire modules 30b-30e may be provided in a kit form. A modular guidewire supply "kit" may include the guidewire modules 30b-30e packaged in sterile trays, sterile containers, etc. as commonly employed for such purposes. The guidewire modules 30b-30e may each be packaged individually, or the guidewire modules 30b-30e may be packaged together. Instructions for use may also be included in the modular guidewire supply kit. Furthermore, the modular guidewire supply kit may include additional guidewire modules 30, allowing surgical staff to determine and select from the modular guidewire supply kit a desired number of guidewire modules 30 to form a modular guidewire. The guidewire modules 30 may be of all the same length or a plurality of lengths.

Figure 4:
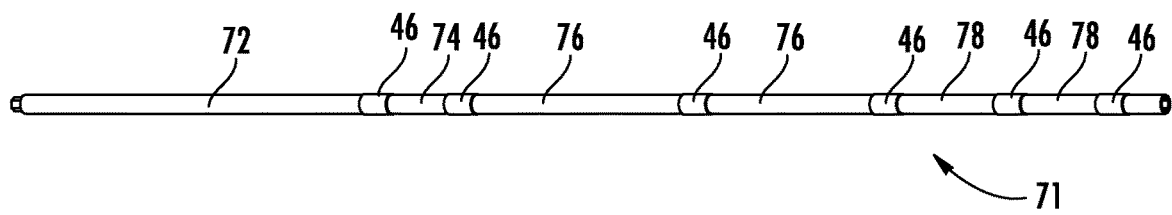
FIG. 4 depicts a plurality of guidewire module embodiments of different lengths, according to an exemplary embodiment, assembled into an embodiment of a modular guidewire.

FIG. 4 illustrates another embodiment of a modular guidewire, shown as modular guidewire 71, including modules of a plurality of lengths. As illustrated in FIG. 4, the modular guidewire 71 is comprised of a plurality of guidewire modules similar to the guidewire module 30 but of different lengths, shown as graded guidewire modules 72, 74, 76, and 78 (with two of the graded guidewire modules 76 and 78 each shown). The graded guidewire module 72 is the longest of the graded guidewire modules shown in FIG. 4, followed in length by the graded guidewire modules 76, the graded guidewire modules 78, and the graded guidewire module 74. The plurality of lengths represented by graded guidewire modules 72, 74, 76, and 78 allow for greater customizability of the length of the modular guidewire 71. As shown in FIG. 4, the graded guidewire modules 72, 74, 76, and 78 are connected together similarly to the guidewire module 30 and the second guidewire module 30a, as shown in FIGS. 2f and 2g. The connections between the graded guidewire modules 72, 74, 76, and 78 are also locked in place by the sleeves 46, though this application also envisions embodiments of the graded guidewire modules 72, 74, 76, and 78 that do not include the sleeves 46. As with guidewire modules 30b-30e from FIG. 3, the graded guidewire modules 72, 74, 76, 78 may be provided in a kit form, along with additional guidewire modules of the same lengths as graded guidewire modules 72, 74, 76, and 78 or of different lengths.

The graded guidewire modules 72, 74, 76, and 78 may be made of a material common to guidewires, such as stainless steel, a high-tensile stainless steel, nitinol, a hybrid of stainless steel and nitinol, etc. A material of a graded guidewire module 72, 74, 76, or 78 may be machined to provide the graded guidewire module 72, 74, 76, or 78 with specific properties (e.g., be micro-cut with grooves to allow for enhanced precision and control). The graded guidewire modules 72, 74, 76, and 78 may also be at least partially covered in a coating, such as a silicone-based coating, a PTFE (polytetrafluoroethylene) coating, a different polymer coating, a hydrophilic coating, a hydrophobic coating, etc. Additionally, the graded guidewire modules 72, 74, 76, and 78 may be designed to be disposable or reusable.

Figure 5A:
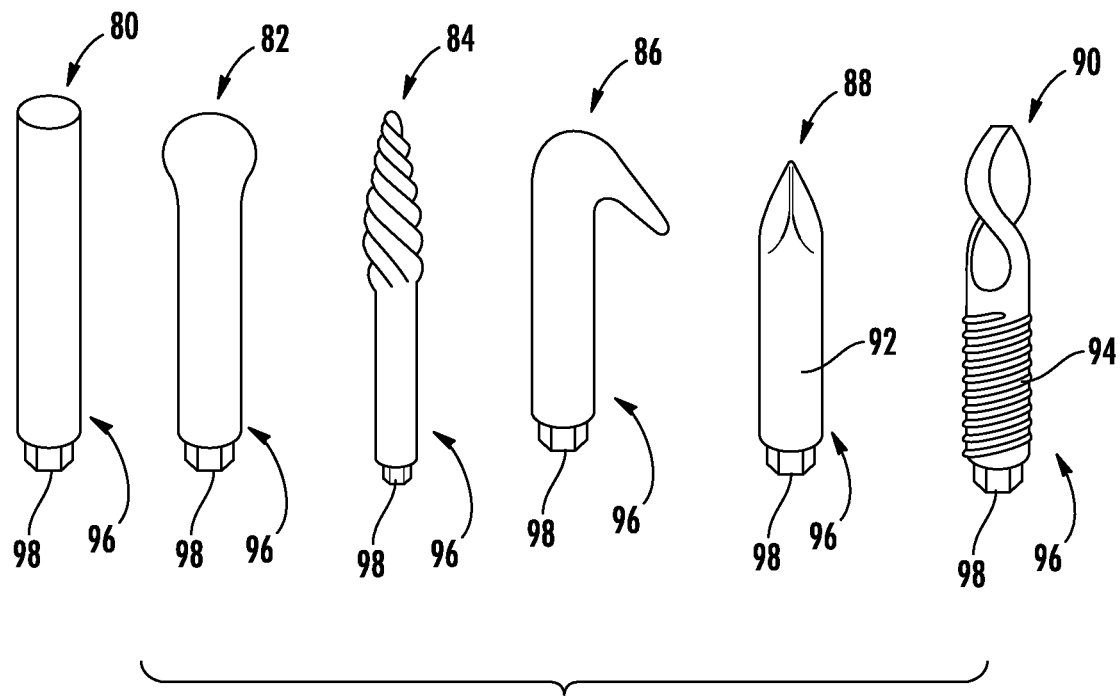
FIG. 5a depicts a plurality of guidewire tip embodiments.

An interchangeable guidewire tip may be attached to one of the ends of a modular guidewire, such as modular guidewire 70 and/or modular guidewire 71. FIG. 5a illustrates example embodiments of these interchangeable guidewire tips: a straight guidewire tip 80, a ball guidewire tip 82, a screw guidewire tip 84, a hooked guidewire tip 86, a trocar guidewire tip 88, and a drill guidewire tip 90. Those of ordinary skill in the art will appreciate that this list of example guidewire tips is not exclusive. Other guidewire tips may be used such as, e.g., a tapered guidewire tip, a diamond guidewire tip (i.e., a guidewire tip with two sides tapering to a diamond-shaped tip), and a radial guidewire tip (i.e., a guidewire tip ending in a partial sphere).

Surgical staff may select an interchangeable guidewire tip to attach to a modular guidewire based on the function the modular guidewire will be performing in the body of a patient during a surgery on a patient. As an example, the surgical staff may select the straight guidewire tip 80 or the ball guidewire tip 82 because the modular guidewire will primarily be navigated through a straight portion of the patient's anatomy. As another example, the surgical staff may select the screw guidewire tip 84 or the hooked guidewire tip 86 because the modular guidewire 70 will be used to remove a broken implant from the patient. As another example, the surgical staff may select the trocar guidewire tip 88 or the drill guidewire tip 90 because the modular guidewire 70 will be used to connect two fragments of a bone of the patient and a sharp tip will allow the modular guidewire to be effectively tapped or drilled into the bone.

Attaching an interchangeable guidewire tip, such as the guidewire tips 80, 82, 84, 86, 88, and 90, to an end of a modular guidewire may be permanent (i.e., the interchangeable guidewire tip cannot be removed once attached). However, in preferred embodiments, interchangeable guidewire tips are configured to be removably attachable to an end of a modular guidewire, such that one interchangeable guidewire tip may be switched out for another interchangeable guidewire tip on the end of the modular guidewire. An advantage of a removably attachable interchangeable guidewire tip is that surgical staff may attach one tip and, after later deciding that the selected tip is unsuitable, switch the tip out for a different tip.

Interchangeable guidewire tips, such as the guidewire tips 80, 82, 84, 86, 88, and 90, may possess a range of characteristics or properties. As an example, interchangeable guidewire tips may possess varying flexibilities, ranging from floppy or soft, to an intermediate flexibility, to stiff or rigid. The flexibility of an interchangeable guidewire tip may be at least partially influenced by a shaping ribbon or coil contained within the interchangeable guidewire tip. As another example, interchangeable guidewire tips may be radio opaque (e.g., because of a platinum coil within the interchangeable guidewire tip) to allow for better visualization via, e.g., fluoroscopy of the modular guidewire 70 to which the interchangeable tip is attached. As shown in FIG. 5a, the interchangeable guidewire tips may also have smooth bases, such as unmachined base 92 of the trocar guidewire tip 88, or the interchangeable guidewire tips may have threaded bases, such as threaded base 94 of the drill guidewire tip 90, to aid in anchoring the interchangeable guidewire tip to an anatomy of a patient (e.g., a bone of the patient).

Interchangeable guidewire tips may be made of a material common to guidewire tips, such as stainless steel, nitinol, a hybrid of stainless steel and nitinol, a shape memory polymer, etc. Interchangeable guidewire tips may further be at least partially covered in a coating, such as a silicone-based coating, a polymer coating, a hydrophilic coating, a hydrophobic coating, etc. Additionally, interchangeable guidewire tips may be magnetic or adhesive, so that the interchangeable guidewire tips may, e.g., facilitate the extraction of a broken implant from a patient. In some embodiments, interchangeable guidewire tips may be disposable, while in other embodiments, interchangeable guidewire tips may be reusable.

As shown in FIG. 5a, each of the guidewire tips 80, 82, 84, 86, 88, and 90 includes a connecting end 96 with an inserting endpiece 98. Thus, the guidewire tips 80, 82, 84, 86, and 90 may connect to an end of a modular guidewire by a connecting process similar to that described with respect to FIGS. 2a-2g above, i.e., by inserting the connecting endpiece 98 into a corresponding, interlocking receiving endpiece of a guidewire module (e.g., the receiving endpiece 44 of the guidewire module 30). Those of ordinary skill in the art will appreciate that the connecting endpieces 98 shown in FIG. 5a, which resemble the inserting endpiece 40 from the guidewire module 30 described with respect to FIGS. 2a-2g, are not meant to be limiting. Rather, this application envisions a variety of designs and configurations for the inserting endpieces 98. Moreover, the connecting ends 96 of the guidewire tips 80, 82, 84, 86, 88, and 90 may include receiving endpieces instead of inserting endpieces 98, the receiving endpieces configured, e.g., similarly to the receiving endpiece 44 of the guidewire module 30.

Figure 5B:
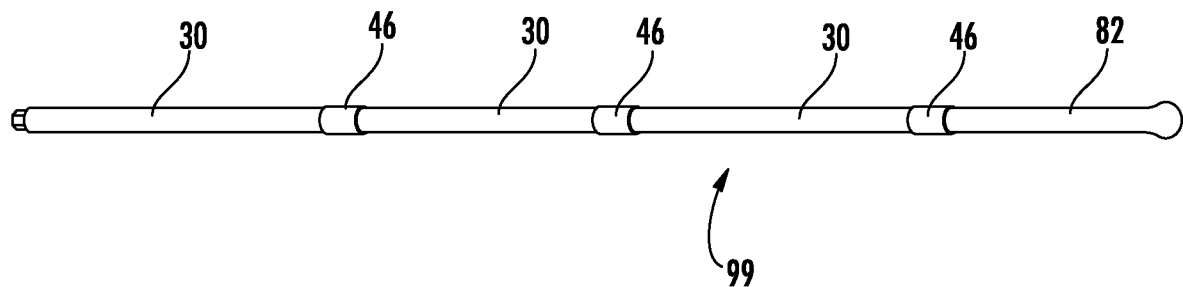

FIG. 5b illustrates an embodiment of a modular guidewire, shown as modular guidewire 99, comprised of a plurality of the guidewire module 30 connected together and connected to the ball guidewire tip 82 from FIG. 5a. As shown in FIG. 5b, the modular guidewire 99 includes sleeves 46 that lock the connections between the guidewire modules 30 and the ball guidewire tip 82. The embodiment of a modular guidewire shown in FIG. 5b is meant to be illustrative rather than limiting, as this application also envisions other configurations of the modular guidewire 99 comprised of differently shaped guidewire tips, differently shaped guidewire modules, differently size guidewire modules, guidewire modules that do not include sleeves, etc.

The guidewire tips 80, 82, 84, 86, 88, and 90 may be provided in a kit form. A modular guidewire supply kit may include one or more of the guidewire tips 80, 82, 84, 86, 88, and 90 packaged in sterile trays, sterile containers, etc. as commonly employed for such purposes. The guidewire tips 80, 82, 84, 86, 88, and 90 may each be packaged individually, or the guidewire tips 80, 82, 84, 86, 88, and 90 may be packaged together. A modular guidewire supply kit may further include one or more guidewire modules, such as guidewire module 30 or graded guidewire modules 72, 74, 76, and 78, along with instructions for use. In some embodiments, a modular guidewire supply kit may contain one guidewire tip and a plurality of the same guidewire module, such as guidewire module 30. In other embodiments, a modular guidewire supply kit may contain one guidewire tip and a plurality of guidewire modules with different lengths, such as the graded guidewire modules 72, 74, 76, and 78. In other preferred embodiments, a modular guidewire supply kit may include a plurality of types of guidewire tips, such as the guidewire tips 80, 82, 84, 86, 88, and 90, along with a plurality of guidewire modules with different lengths, such as graded guidewire modules 72, 74, 76, and 78. Thus, surgical staff may form a modular guidewire, such as the modular guidewire 99 shown in FIG. 5b, by selecting a guidewire tip and a plurality of guidewire modules from a modular guidewire supply kit.

Figure 6A:
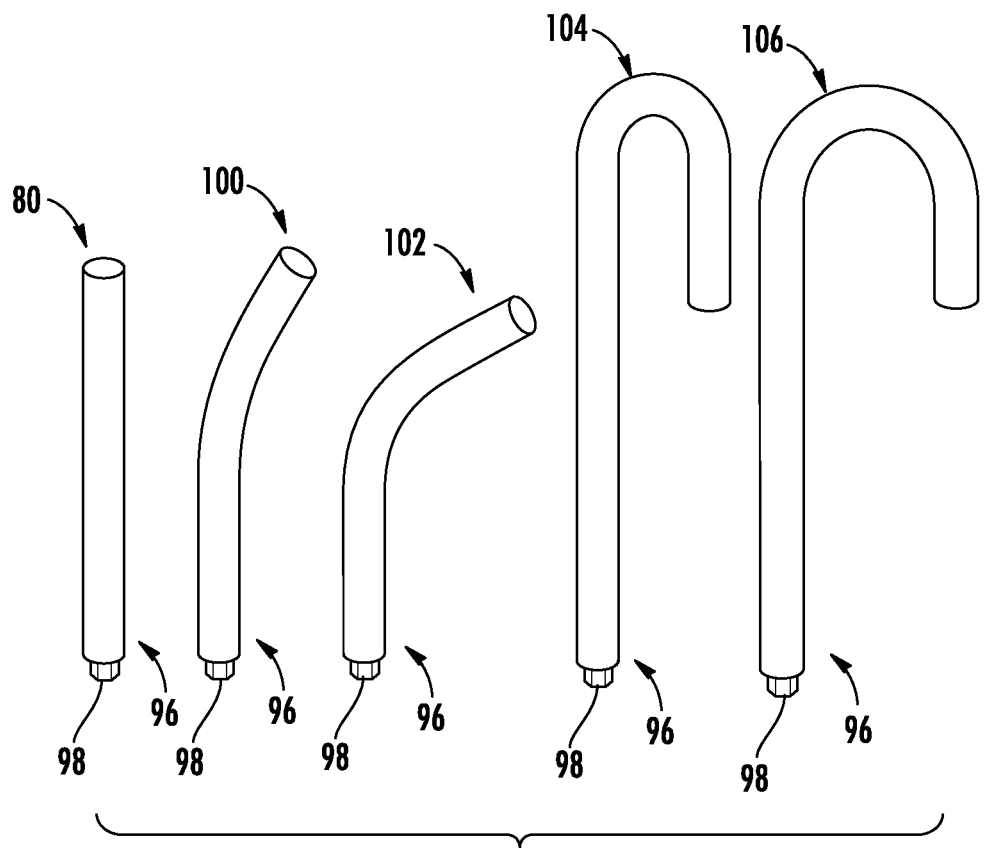
FIG. 6a depicts a plurality of guidewire tip embodiments.

In contrast to the interchangeable guidewire tips shown in FIG. 5a, an interchangeable guidewire tip with a particular shape may alternatively be attached to one of the ends of a modular guidewire, such as modular guidewires 70, 71, and/or 99. FIG. 6a illustrates a plurality of shaped interchangeable guidewire tips, shown as straight guidewire tip 80, slightly bent guidewire tip 100, moderately bent guidewire tip 102, small J-curved guidewire tip 104, and large J-curved guidewire tip 106. Those of ordinary skill in the art will appreciate that this list of example shaped guidewire tips is not exclusive of shaped guidewire tips. Other shaped guidewire tips may be used such as, e.g., a double curved guidewire tip or a non-symmetrical J-curved guidewire tip.

As with guidewire tips 80, 82, 84, 86, 88, and 90 shown in FIGS. 5a and 5b, surgical staff may select an interchangeable guidewire tip with a particular shape, such as the shaped guidewire tips 80, 100, 102, 104, and 106 shown in FIG. 6a, to attach to a modular guidewire based on the function the modular guidewire will be performing in the body of a patient during surgery. As an example, the surgical staff may select the slightly bent guidewire tip 100 or the moderately bent guidewire tip 102 to aid them in maneuvering the modular guidewire through a tortuous vasculature of the patient. As another example, the surgical staff may select the small J-curved guidewire tip 104 or the large J-curved guidewire tip 106 to aid them in guiding the modular guidewire into a particular aortic branch of the patient.

Interchangeable guidewire tips of different shapes, such as the shaped guidewire tips 80, 100, 102, 104, and 106, may possess a range of characteristics or properties, similar to those described above with respect to guidewire tips 80, 82, 86, 88, and 90 from FIG. 5a. As examples, shaped interchangeable guidewire tips may possess various flexibilities, may be radio opaque, and may have smooth or threaded bases. Interchangeable guidewire tips may also possess a combination of characteristics from the guidewire tips 80, 82, 84, 86, 88, and 99 shown in FIG. 5a and the shaped guidewire tips 80, 100, 102, 104, and 106 shown in FIG. 6a. As an example, an interchangeable guidewire tip may be a bent trocar tip that is of intermediate flexibility and includes a threaded base. As another example, an interchangeable guidewire tip may be a large J-curved ball tip that is of soft flexibility and is radio opaque.

Shaped interchangeable guidewire tips may be made of a material common to guidewire tips, such as stainless steel, nitinol, a hybrid of stainless steel and nitinol, a shape memory polymer, etc. Shaped interchangeable guidewire tips may further be at least partially covered in a coating, such as a silicone-based coating, a polymer coating, a hydrophilic coating, a hydrophobic coating, etc. Additionally, shaped interchangeable guidewire tips may be magnetic or adhesive, so that the shaped interchangeable guidewire tips may, e.g., facilitate the extraction of a broken implant from a patient. In some embodiments, shaped interchangeable guidewire tips may be disposable, while in other embodiments, shaped interchangeable guidewire tips may be reusable.

As shown in FIG. 6a, and similar to the guidewire tips 80, 82, 84, 86, 88, and 90 shown in FIG. 5a, each of the guidewire tips 80, 100, 102, 104, and 106 includes a connecting end 96 with an inserting endpiece 98. Thus, the shaped guidewire tips 80, 100, 102, 104, and 106 may connect to an end of a modular guidewire by a connecting process similar to that described with respect to FIGS. 2a-2g above, i.e., by inserting the connecting endpiece 98 into a corresponding, interlocking receiving endpiece of a guidewire module (e.g., the receiving endpiece 44 of the guidewire module 30). Those of ordinary skill in the art will appreciate that the connecting endpieces 98 shown in FIG. 6a are not meant to be limiting. Rather, this application envisions a variety of designs and configurations for the connecting endpieces 98. Moreover, the connecting ends 96 of the shaped guidewire tips 80, 100, 102, 104, and 106 may include receiving endpieces instead of inserting endpieces 98, the receiving endpieces configured, e.g., similarly to the receiving endpiece 44 of the modular guidewire 30.

Figure 6B:
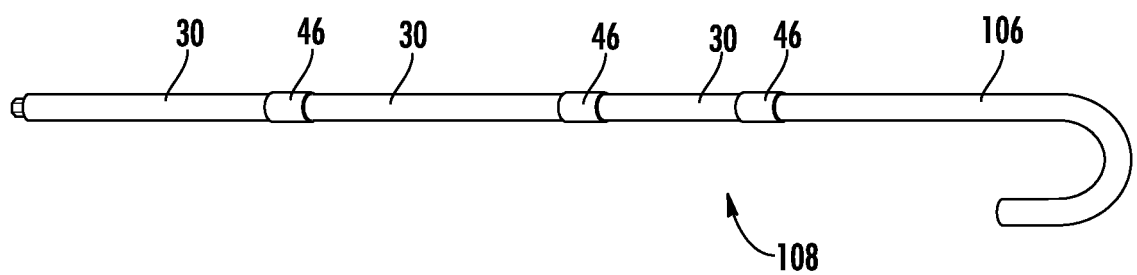

FIG. 6b illustrates an embodiment of a modular guidewire, shown as modular guidewire 108, comprised of a plurality of the guidewire module 30 connected together and connected to the large J-curved guidewire tip 106 from FIG. 6a. As shown in FIG. 6b, the modular guidewire 108 includes sleeves 46 that lock the connections between the guidewire modules 30 and the ball guidewire tip 82. The embodiment of a modular guidewire shown in FIG. 6b is meant to be illustrative rather than limiting, as this application also envisions other configurations of the modular guidewire 99 comprised of differently shaped guidewire tips, differently shaped guidewire modules, differently size guidewire modules, guidewire modules that do not include sleeves, etc.

As with the guidewire tips 80, 82, 84, 86, 88, and 90 from FIGS. 5a and 5b, the shaped modular guidewire tips 80, 100, 102, 104, and 106 may be provided in a kit form. A modular guidewire supply kit may include one or more of the guidewire tips 80, 82, 84, 86, 88, and 90 and/or the shaped guidewire tips 80, 100, 102, 104, 106 packaged, individually or together, in sterile trays, sterile containers, etc. as commonly employed for such purposes. In some embodiments, a modular guidewire supply kit may additionally or alternatively include one or more interchangeable guidewire tips that combine characteristics of the interchangeable guidewire tips from FIG. 5a and FIG. 6a (e.g., an interchangeable guidewire tip that is a bent trocar tip of intermediate flexibility). A modular guidewire supply kit may further include one or more guidewire modules, such as guidewire module 30 or graded guidewire modules 72, 74, 76, and 78, along with instructions for use. Thus, surgical staff may form a modular guidewire, such as the modular guidewire 108 from FIG. 6b, by selecting a guidewire tip and a plurality of guidewire modules from a modular guidewire supply kit.

Figure 7A:
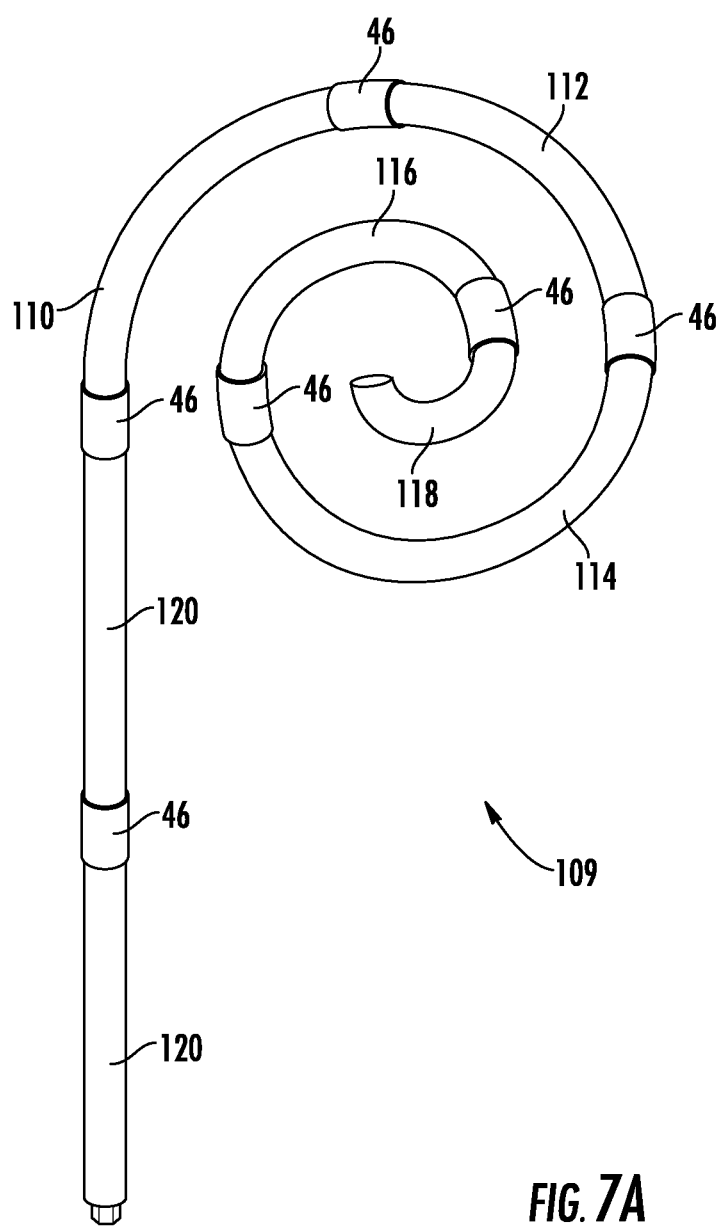
FIG. 7a depicts an embodiment of a modular guidewire including shaped guidewire modules.

However, the guidewire tips are not the only modular guidewire components that may be shaped. Shaped guidewire modules may also or alternatively be included in a modular guidewire depending on the modular guidewire's intended use. FIG. 7a illustrates an embodiment of a modular guidewire, shown as double-curved modular guidewire 109, the curved modular guidewire including embodiments of shaped guidewire modules, shown as curved guidewire modules 110, 112, 114, and 116. As shown in FIG. 7a, the curved guidewire modules 110, 112, 114, and 116 of the double-curved modular guidewire 109 are connected together to form a chain. The chain of the curved guidewire modules 110, 112, 114, and 116 is attached to a short, J-curved guidewire tip 118 at one end and straight guidewire modules 120 at the other end. Each connection between the curved guidewire modules 110, 112, 114, 116, the short, J-curved guidewire tip 118, and the straight guidewire modules 120 is locked into place by a sleeve 46. However, embodiments of modular guidewires without sleeves 46 or other methods of locking connections into place are also envisioned by this application.

Moving from the curved guidewire module 110 to the curved guidewire module 116, the curved guidewire modules 110, 112, 114, and 116 become increasingly curved, such that when the guidewire modules 110, 112, 114, and 116 are connected together and to the short, J-curved guidewire tip 118, they form a double-curved of the double-curved modular guidewire 109. However, the curved guidewire modules 110, 112, 114, and 116 are designed in such a way that surgical staff may choose not to connect all of the curved guidewire modules 110, 112, 114, and 116. As an example, surgical staff may decide that a double curved modular guidewire is not necessary and only connect the curved guidewire modules 110 and 112 and the short, J-curved guidewire tip 118 to form a single-curved modular guidewire. As another example, the surgical staff may decide that a more tightly curved modular guidewire is needed and connect curved guidewire modules 114 and 116 and the short, J-curved guidewire tip 118 to form a tight single-curved modular guidewire. Additionally or alternatively, the surgical staff may select a guidewire tip different from the short, J-curved guidewire tip 118, such as one of the guidewire tips from FIG. 5a or FIG. 6a, to attach to the curved guidewire modules 110, 112, 114, and 116.

Figure 7B:
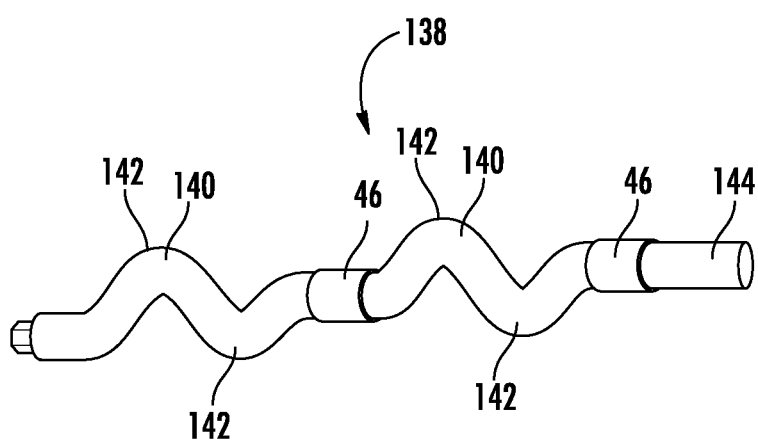
FIG. 7b depicts an embodiment of a modular guidewire including shaped guidewire modules.

FIG. 7b illustrates another embodiment of a modular guidewire, shown as undulating modular guidewire 138, including embodiments shaped guidewire modules, shown as undulating guidewire modules 140. Each of the undulating guidewire modules 140 includes U-curved portions 142, which give them the appearance of "undulation." As shown in FIG. 7b, the undulating guidewire modules 140 are connected to a straight guidewire tip 144, though in other embodiments the undulating guidewire modules 140 may be connected to a different guidewire tip, such as one of the guidewire tips from FIG. 5a or FIG. 6a. Each connection between the undulating guidewire modules 140 and the straight guidewire tip 144 is secured with a sleeve 46 in the undulating modular guidewire 138, but other embodiments without sleeves 46 are also envisioned by this application.

FIGS. 7a and 7b are intended to be illustrations of shaped guidewire modules, but they are not limiting. This application also anticipates other shaped guidewire modules, such as helix-shaped guidewire modules and bent guidewire modules. Alternatively, surgical staff may "shape" an otherwise straight modular guidewire by contouring the modular guidewire before performing a surgical operation. The surgical staff may contour the modular guidewire in order to create a specific shape in the modular guidewire for achieving an immediate need (e.g., creating a hooked or bent shape that will aid the surgeon in locating and/or extracting a canal of a fragment of a fractured implant). As with the guidewire module 30 and the graded guidewire modules 72, 74, 76, and 78, shaped guidewire modules, such as the curved guidewire modules 110, 112, 114, and 116 and/or the undulating guidewire modules 140, may be provided in a kit form.

Figure 8A:
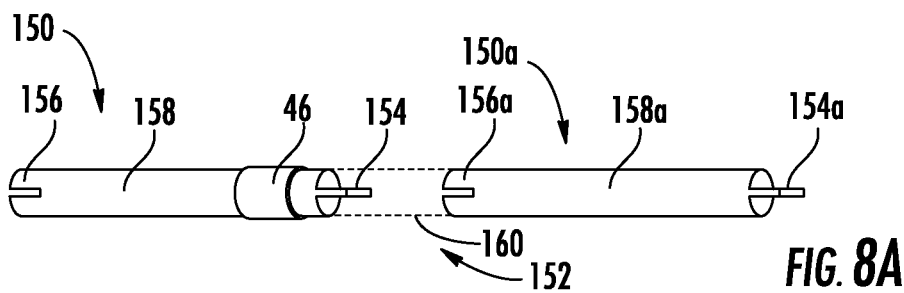
FIG. 8a depicts two guidewire modules according to a second exemplary embodiment.
Figure 8B:
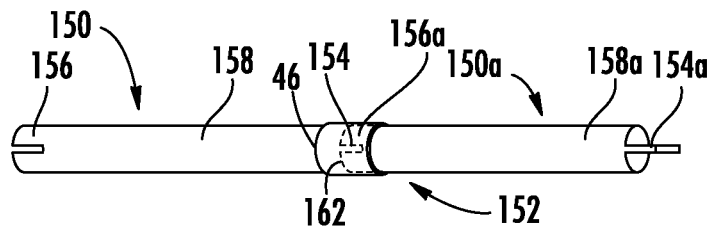
FIG. 8b depicts the two of the of the guidewire modules embodied in FIG. 8a, connected together.

FIGS. 8a-8f show a plurality of embodiments of guidewire module endpieces. FIGS. 8a and 8b illustrate modular guidewire embodiments, shown as sliding guidewire modules 150 and 150a. A sliding plate endpiece system 152 is defined by the two sliding guidewire modules 150 and 150a. As shown in FIG. 8a, the sliding plate endpiece system 152 comprises an inserting endpiece 154 of the sliding guidewire module 150 and a receiving endpiece 156a of the sliding guidewire module 152a. The inserting endpiece 154 is a narrow, rectangular plate that extends from a body 158 of the sliding guidewire module 150. The receiving endpiece 156a is a recess within a body 158a of the guidewire modules 150a. The receiving endpiece 156a is configured to be interlocking with the inserting endpiece 154 such that the narrow rectangular plate of the inserting endpiece 154 may slide into the receiving endpiece 156, following an insertion path shown by dashed lines 160. In this way, the sliding guidewire modules 150 and 150a may be connected. Of course, the sliding endpiece system may alternatively be comprised of an inserting endpiece 154a of the sliding guidewire module 150a and a receiving endpiece 156 of the sliding guidewire module 150, the inserting endpiece 154a configured similarly to the inserting endpiece 154 and the receiving endpiece 156 configured similarly to the receiving endpiece 156a. Thus, the sliding guidewire modules 150 and 150a may alternatively be connected by sliding the inserting endpiece 154a into the receiving endpiece 156.

FIG. 8b shows the sliding guidewire modules 150 and 150a connected together via an interlocking connection, shown as connection 162, between the inserting endpiece 154 of the sliding guidewire module 150 and the receiving endpiece 156a of the sliding guidewire module 150a. The connection 162 between the inserting endpiece 154 and the receiving endpiece 156a limits rotation and separation between the sliding guidewire modules 150 and 150a by, e.g., friction between the inserting endpiece 154 and the receiving endpiece 156a and/or a shape of the receiving endpiece 156a holding the inserting endpiece 154 in place. In the embodiment of FIG. 8b, a sleeve 46 of the sliding guidewire module 150 has been threaded over the connection 162. The sleeve 46 further prevents rotation and separation between the sliding guidewire modules 150 and 150a, essentially "locking" the sliding guidewire modules 152 and 152a together in a rigid fashion. However, this application also envisions configurations of sliding guidewire modules 152 and 152a that do not include a sleeve 46.

Figure 8C:
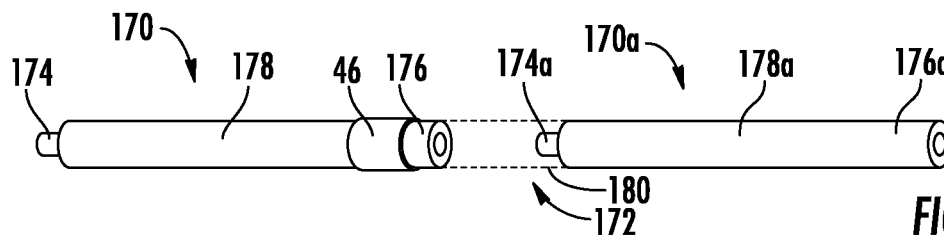
FIG. 8c depicts two guidewire modules according to a third exemplary embodiment.
Figure 8D:
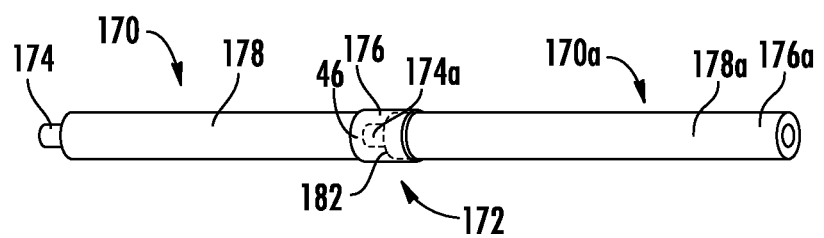
FIG. 8d depicts the two of the of the guidewire modules embodied in FIG. 8c, connected together.

FIGS. 8c and 8d illustrate modular guidewire embodiments, shown as pin guidewire modules 170 and 170a. A pin endpiece system 172 is defined by the two pin guidewire modules 170 and 170a. As shown in FIG. 8c, the pin endpiece system 172 comprises an inserting endpiece 174a of the pin guidewire module 170a and a receiving endpiece 176 of the pin guidewire module 170. The inserting endpiece 174a is a short cylindrical "pin" that extends from a body 178a of the guidewire module 172a. The receiving endpiece 176 is a cylindrical recess within a body 178 of the pin guidewire module 170. The receiving endpiece 176 is configured to be interlocking with the inserting endpiece 174a such that the cylindrical pin of the pin inserting endpiece 174a may slide into the receiving endpiece 176, following an insertion path shown by dashed lines 180. In this way, the pin guidewire modules 170 and 170a may be connected. Of course, the pin endpiece system 172 may alternatively be comprised of an inserting endpiece 174 of the pin guidewire module 170 and a receiving endpiece 176a of the pin guidewire module 170a, the inserting endpiece 174 configured similarly to the inserting endpiece 174a and the receiving endpiece 176a configured similarly to the receiving endpiece 176. Thus, the pin guidewire modules 170 and 170a may alternatively be connected by sliding the inserting endpiece 174 into the receiving endpiece 176a.

FIG. 8d shows the pin guidewire modules 170 and 170a connected together via an interlocking connection, shown as connection 182, between the inserting endpiece 174a of the pin guidewire module 170a and the receiving endpiece 174 of the pin guidewire module 170. The connection 182 between the inserting endpiece 174a and the receiving endpiece 176 limits rotation and separation between the pin guidewire modules 170 and 170a by, e.g., friction between the inserting endpiece 174a and the receiving endpiece 176. In the embodiment of FIG. 8d, a sleeve 46 of the pin guidewire module 170 has been threaded over the connection 182. The sleeve 46 further prevents rotation and separation between the pin guidewire modules 170 and 170a, essentially "locking" the pin guidewire modules 170 and 170a together in a rigid fashion. However, this application also envisions configurations of the pin guidewire modules 170 and 170a that do not include a sleeve 46.

Figure 8E:
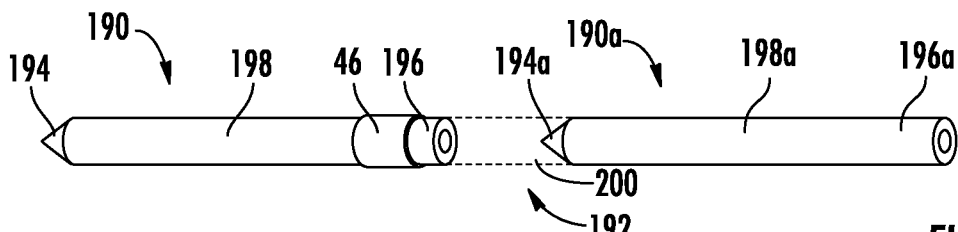
FIG. 8e depicts two guidewire modules according to a fourth exemplary embodiment.
Figure 8F:
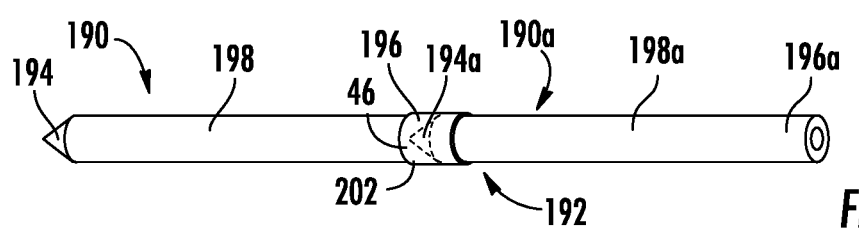
FIG. 8f depicts the two of the of the guidewire modules embodied in FIG. 8e, connected together.

FIGS. 8e and 8f illustrate modular guidewire embodiments, shown as pointed guidewire modules 190 and 190a. A pointed endpiece system 192 is defined by the two pointed guidewire modules 190 and 190a. As shown in FIG. 8e, the pointed endpiece system 192 comprises an inserting endpiece 194a of the pointed guidewire module 190a and a receiving endpiece 196 of the pointed guidewire module 190. The inserting endpiece 194a is a pointed cone extending from a body 198a of the pointed guidewire module 190a. The receiving endpiece 196 is a conical recess within a body 198 of the pointed guidewire module 190. The receiving endpiece 196 is configured to be interlocking with the inserting endpiece 194a such that the pointed cone of the inserting endpiece 194a may slide into the receiving endpiece 196, following an insertion path shown by dashed line 200. In this way, the pointed guidewire modules 190 and 190a may be connected. Of course, the pointed endpiece system 192 may alternatively be comprised of a, inserting endpiece 194 of the pointed guidewire module 190 and a receiving endpiece 196a of the pointed guidewire module 190a, the inserting endpiece 194 configured similarly to the inserting endpiece 194a and the receiving endpiece 196a configured similarly to the receiving endpiece 196. Thus, the pointed guidewire modules 190 and 190a may alternatively be connected by sliding the inserting endpiece 194 into the receiving endpiece 196a.

FIG. 8f shows the pointed guidewire modules 190 and 190a connected together via an interlocking connection, shown as connection 202, between the inserting endpiece 194a of the pointed guidewire module 190a and the receiving endpiece 196 of the pointed guidewire module 190. The connection 202 between the inserting endpiece 194a and the receiving endpiece 196 limits rotation between the pointed guidewire modules 190 and 190a by, e.g., friction between the inserting endpiece 194a and the receiving endpiece 196. In the embodiment of FIG. 8f, a sleeve 46 of the pointed guidewire module 190 has been threaded over the connection 202. The sleeve 46 further prevents rotation and separation between the pointed guidewire modules 190 and 190a, essentially "locking" the pointed guidewire modules 190 and 190a together in a rigid fashion. However, this application also envisions configurations of the pointed guidewire modules 190 and 190a that do not include a sleeve 46.

Figure 9A:
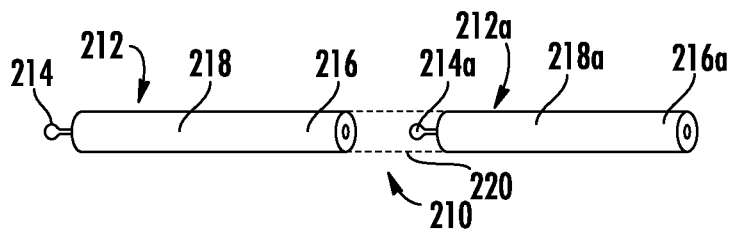
FIG. 9a depicts two guidewire modules according to a fifth exemplary embodiment.
Figure 9B:
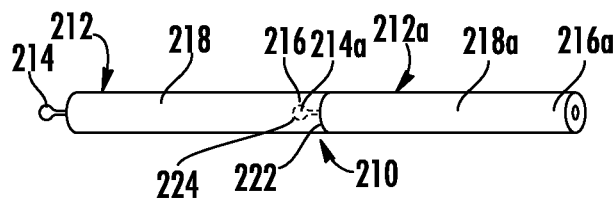
FIG. 9b depicts the two of the of the guidewire modules embodied in FIG. 9a, connected together.

FIGS. 9a-9d show a plurality of embodiments of guidewire module endpieces that do not include a sleeve to "lock" them together. FIGS. 9a and 9b illustrate modular guidewire embodiments, shown as "snapping" guidewire modules 210 and 210a. A "snapping" endplate system 212 is defined the two snapping guidewire modules 210 and 210a. As shown in FIG. 9a, the snapping endpiece system 212 comprises an inserting endpiece 214a of the snapping guidewire module 210a and a receiving endpiece 216 of the snapping guidewire module 210. The inserting endpiece 214a comprises a cylindrical peg with a larger, spherical tip extending from a body 218a of the snapping guidewire module 210a. The receiving endpiece 216 is a cylindrical recess within a body 218 of the snapping guidewire modules 210, the cylindrical recess having a larger, spherical shaped to fit the larger, spherical tip of the inserting endpiece 214a. The receiving endpiece 216 is configured to be interlocking with the inserting endpiece 214a such that the peg of the inserting endpiece 214a may slide into the receiving endpiece 216, following an insertion path shown by dashed line 220. Once the inserting endpiece 214a is slid into the receiving endpiece 216, the larger, spherical tip of the inserting endpiece 214a becomes fastened into the larger spherical bottom of the receiving endpiece 216. In other words, sliding the peg of the inserting endpiece 214a into the receiving endpiece 216 "snaps" the snapping guidewire modules 210 and 210a together. In this way, the snapping guidewire modules 210 and 210a may be connected. Of course, the snapping endpiece system 212 may alternatively be comprised of an inserting endpiece 214 of the snapping guidewire module 210 and a receiving endpiece 216a of the snapping guidewire module 210a, the inserting endpiece 214 configured similarly to the inserting endpiece 214a and the receiving endpiece 216a configured similarly to the receiving endpiece 216. Thus, the snapping guidewire modules 210 and 210a may alternatively be connected snapping the inserting endpiece 214 into the receiving endpiece 216a.

FIG. 9b shows the snapping guidewire modules 210 and 210a connected together via an interlocking connection, shown as connection 222, between the inserting endpiece 214 and the receiving endpiece 216. A dashed line 224 shows the inserting endpiece 214a snapped into the receiving endpiece 216. The connection 222 between the inserting endpiece 214a and the receiving endpiece 216 limits rotation between the snapping guidewire modules 210 and 210a by, e.g., friction between the inserting endpiece 214a and the receiving endpiece 216. The connection 222 further limits separation between the snapping guidewire modules 210 and 210a because the larger, spherical tip of the inserting endpiece 214a, as fastened into the receiving endpiece 216, prevents the connection 222 between the snapping guidewire modules 210 and 210a from being easily disrupted (e.g., without the application of at least moderate force). In this way, the snapping endpiece system 212 essentially "locks" the snapping guidewire modules 210 and 210a together in a rigid fashion.

Figure 9C:
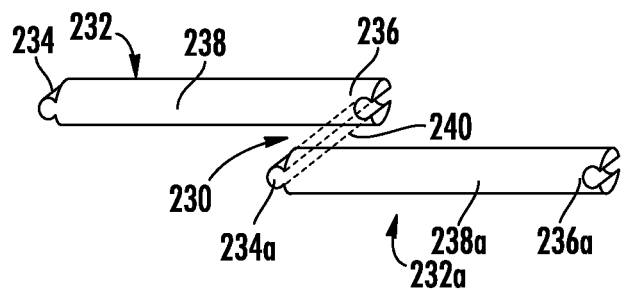
FIG. 9c depicts two guidewire modules according to a fourth exemplary embodiment.
Figure 9D:
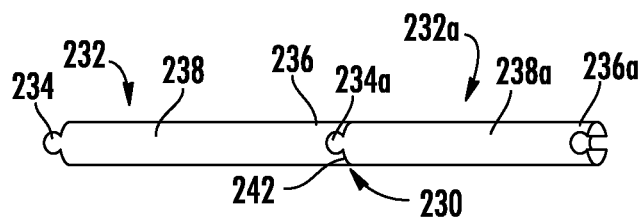
FIG. 9d depicts the two of the of the guidewire modules embodied in FIG. 9c, connected together.

FIGS. 9c and 9d illustrate modular guidewire embodiments, shown as "sliding peg" guidewire modules 230 and 230a. A "sliding peg" endpiece system 232 is defined the two sliding peg guidewire modules 230 and 230a. As shown in FIG. 9c, the sliding peg endpiece system 232 comprises an inserting endpiece 234a of the sliding peg guidewire module 230a and a receiving endpiece 236 of the sliding peg guidewire module 230. The inserting endpiece 234a comprises a round, roughly cylindrical peg extending from a body 238a of the sliding peg guidewire module 230a. The receiving endpiece 236 comprises a round socket extending from a side of a body 238 of the sliding peg guidewire modules 230 to the other side the body 238. The receiving endpiece 236 is configured to be interlocking with the inserting endpiece 234a such that the peg of the inserting endpiece 234a may slide into the receiving endpiece 236 from a side of the body 238 of the sliding peg guidewire module 230, following an insertion path shown by dashed lines 240. In this way, the sliding peg guidewire modules 230 and 230a may be connected. Of course, the sliding peg endpiece system 232 may alternatively be comprised of an inserting endpiece 234 of the sliding peg guidewire module 230 and a receiving endpiece 236a of the sliding peg guidewire module 230a, the inserting endpiece 234 configured similarly to the inserting endpiece 234a and the receiving endpiece 236a configured similarly to the receiving endpiece 236. Thus, the sliding peg guidewire modules 230 and 230a may alternatively be connected by sliding the inserting endpiece 234 into the receiving endpiece 236a.

FIG. 9d shows the sliding peg guidewire modules 230 and 230a connected together via an interlocking connection, shown as connection 242, between the inserting endpiece 234a and the receiving endpiece 236. The connection 242 between the inserting endpiece 234a and the receiving endpiece 236 limits rotation between the sliding peg guidewire modules 230 and 230a by, e.g., friction between the inserting endpiece 234a and the receiving endpiece 236 and/or a shape of the receiving endpiece 236 holding the inserting endpiece 234a in place. The connection 242 further limits separation between the sliding peg guidewire modules 230 and 230a, as the round peg of the inserting endpiece 234a is larger than an opening of the receiving endpiece 236 that faces the end of the sliding peg guidewire module 230. As such, separation between the sliding peg guidewire modules 230 and 230a is unlikely to occur even if, e.g., moderate force is applied to the ends of the connected sliding peg guidewire modules 230 and 230a. Rather, the primary means to separate the sliding peg guidewire modules 230 and 230a is by sliding the sliding peg guidewire modules 230 and 230a apart, back along the insertion path shown by the dashed lines 240 from FIG. 9c. In this way, the sliding peg endpiece system 232 essentially "locks" the sliding peg guidewire modules 230 and 230a together in a rigid fashion because, e.g., the connection 242 is tight between the sliding peg guidewire modules 230 and 230a and friction prevents regular sliding forces from separating the sliding peg guidewire modules 230 and 230a along the insertion path 240.

Figure 10:
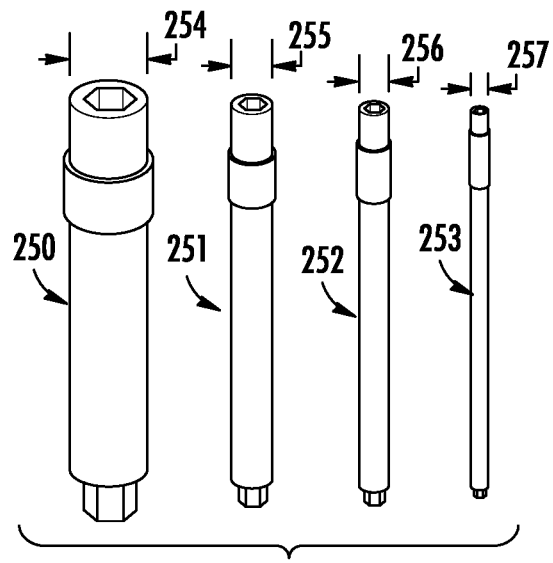
FIG. 10 depicts a plurality of guidewire modules, each with a different diameter, according to an exemplary embodiment.

As shown in FIG. 10, guidewire modules may be of varying diameters. FIG. 10 illustrates four embodiments of a guidewire module, each embodiment having a differently sized diameter, shown as wide guidewire module 250, intermediate guidewire module 251, narrow guidewire module 252, and very narrow guidewire module 253. A diameter 254 of the wide guidewire module 250 is larger than a diameter 255 of the intermediate guidewire module 251, which in turn is larger than a diameter 256 of the narrow guidewire module 252. Further, the diameter 256 of the narrow guidewire module is larger than a diameter 257 of the very narrow guidewire modules 253. Typically, diameters of guidewire range from 1.0 mm to 3.2 mm. As such, in some embodiments, the diameter 254 of the wide guidewire module 250 may range up to 3.2 mm, with the diameter 255 of the intermediate guidewire module 251, the diameter 256 of the narrow guidewire module 252, and the diameter 257 of the very narrow guidewire module 253 being less than 3.2 mm in equal increments (e.g., the intermediate guidewire module 252 having a diameter 255 of 2.7 mm, the narrow guidewire module 254 having a diameter 256 of 2.2 mm, and the very narrow guidewire module 256 having a 257 diameter of 1.7 mm). In other embodiments, the diameter 257 of the very narrow guidewire module 253 may range down to 1.0 mm, with the diameter 256 of the narrow guidewire module 252, the diameter 255 of the intermediate guidewire module 251, and the diameter 254 of the wide guidewire module 250 being greater than 1.0 mm in unequal increments (e.g., the narrow guidewire module having a diameter 256 of 1.7 mm, the intermediate guidewire having a diameter 255 of 2.0 mm, and the large guidewire module having a diameter 254 of 3.1 mm). As such, in certain embodiments, the guidewire modules have a diameter between 1.0 mm and 3.2 mm.

Additionally, in some embodiments, a modular guidewire supply kit may include guidewire modules of varying diameters, such as the wide guidewire module 250, the intermediate guidewire module 251, the narrow guidewire module 252, and the very narrow guidewire module 253. In such embodiments, surgical staff may select which diameter of guidewire module would be most suitable to the guidewire application before them. In other embodiments, however, a modular guidewire supply kit may include guidewire modules of only one diameter.

Figure 11A:
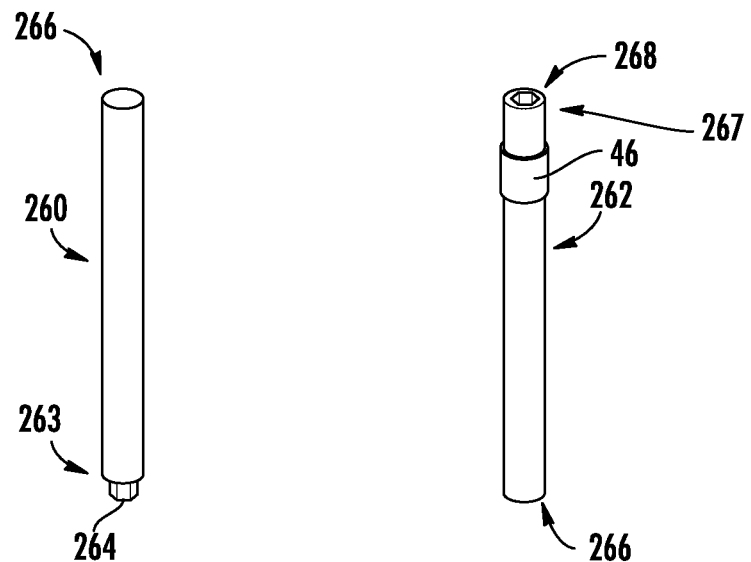
FIG. 11a depicts embodiments of endcap guidewire modules.

As shown in FIGS. 11a-11d, a modular guidewire may include a guidewire module that serves as an "endcap" to the modular guidewire. FIG. 11a illustrates embodiments of endcap guidewire modules, shown as top endcap guidewire module 260 and bottom endcap guidewire module 262. Endcap guidewire modules may be configured such that they include only one connecting endpiece; as an example and as shown in FIG. 11a, the top endcap guidewire module 260 has only one connecting end, shown as connecting end 263, and only one connecting endpiece, shown as inserting endpiece 264. The other end of the top endcap guidewire module 260 is a flat end, shown as non-connecting end 266. Thus, the top endcap guidewire module 260 may attach to a chain of guidewire modules by a connection between the inserting endpiece 264 and a receiving endpiece of the chain of guidewire modules. However, once attached, the non-connecting end 266 of the top endcap guidewire module 260 prevents further guidewire modules from attaching to the top endcap guidewire module 260. Instead, the top endcap guidewire module 260 serves as a "cap" to end the chain of guidewire modules.

Similarly, the bottom endcap guidewire module 262 has only one connecting endp, shown as connecting end 267, and only one connecting endpiece, shown as receiving endpiece 268. The other end of the bottom endcap guidewire module is a flat end, also shown as non-connecting end 266. The bottom endcap guidewire module 262 may attach to a chain of guidewire modules by a connection between the receiving endpiece 268 and an inserting endpiece of the chain of guidewire modules, with the sleeve 46, in some embodiments, configured to thread over this connection and limit rotation and/or separation between the bottom endcap guidewire module 262 and the chain of guidewire modules. As with the top endcap guidewire module 260, once attached, the non-connecting end 266 of the bottom endcap guidewire module 262 prevents further guidewire modules from attaching, and instead the bottom guidewire module 262 serves as a "cap" to end the chain of guidewire modules.

It may be desirable to use an endcap guidewire module, such as the top endcap guidewire module 260 and/or the bottom endcap guidewire module 262, to end a chain of guidewire modules because the non-connecting ends 266 may provide a smooth ending to the chain of guidewire modules. The smooth ending produced from the non-connecting ends 266 may, e.g., prevent an end of the chain of guidewire modules from catching on undesirable objects. The flat ends 266 shown in FIG. 11a are meant to be illustrative. Other designs that provide a non-connecting ending to a guidewire module and accomplish these same functions are also envisioned such as, e.g., a radial ending (i.e., an endcap guidewire module with a non-connecting end shaped as a half-sphere).

Figure 11B:
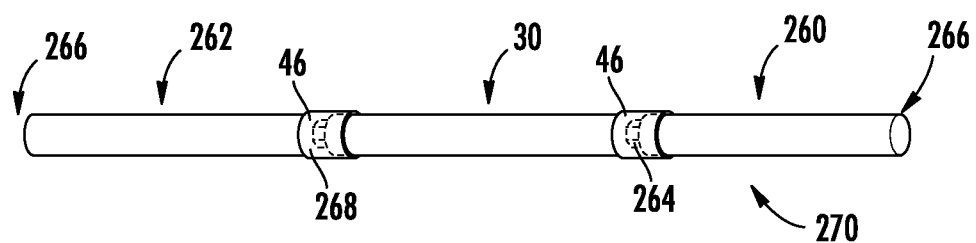

FIG. 11b illustrates an embodiment of a modular guidewire, shown as capped modular guidewire 270. The capped modular guidewire 270 includes the top endcap guidewire module 260 and the bottom endcap guidewire module 262 from FIG. 11a. As shown in FIG. 11b, the non-connecting ends 266 end, or "cap," the capped modular guidewire 270 such that the capped modular guidewire 270 does not include exposed connecting endpieces. This is in contrast to, e.g., the modular guidewire 70 shown in FIG. 3 and the modular guidewire 71 shown in FIG. 4.

As shown in FIG. 11b, the top endcap guidewire module 260 may be connected to a guidewire module, such as guidewire module 30, by the inserting endpiece 264. Similarly, the bottom endcap guidewire module 262 may be connected to a guidewire module, such as guidewire module 30, by the receiving endpiece 268. In the embodiment shown in FIG. 11b, the connections between the top endcap guidewire module 260, the bottom endcap guidewire module 262, and the guidewire module 30 are secured with sleeves 46, which aid in preventing rotation and separation at the connections. However, embodiments that do not include sleeves 46, or which include different inserting endpiece and receiving endpiece designs, are also envisioned. Additionally, although not shown in FIG. 11b, the capped modular guidewire 270 may be assembled such that it includes more than one guidewire module between the top endcap guidewire module 260 and the bottom endcap guidewire module 262.

Figure 11C:
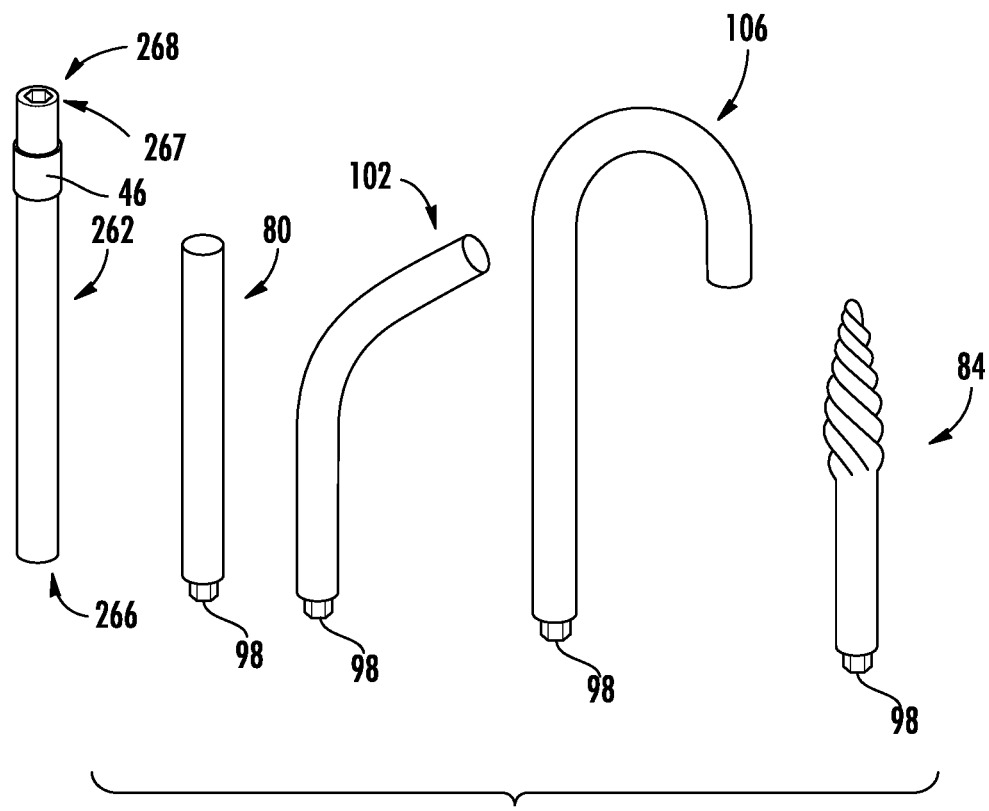
FIG. 11c depicts an embodiment of an endcap guidewire module and a plurality of guidewire tip embodiments.

Alternatively, a modular guidewire may include an endcap guidewire module at one end and a guidewire tip at the other end; FIG. 11c illustrates an example of a guidewire endcap module and guidewire tips that a surgical staff may select from in building such a modular guidewire. Shown in FIG. 11c is the bottom endcap guidewire module 262 and a plurality of guidewire tips from FIGS. 5a and 6a, specifically the straight guidewire tip 80, the moderately bent guidewire tip 102, the large J-curved guidewire tip 106, and the screw guidewire tip 84. In the embodiment of FIG. 11c, the bottom endcap guidewire module 262 includes the receiving endpiece 268 configured to attach to an inserting endpiece, and the each of plurality of guidewire tips 80, 102, 106, and 84 includes an inserting endpiece 98 configured to attach to a receiving endpiece. However, the configurations of these endpieces may be altered to include different connecting endpiece designs or arrangements. As an example, the bottom endcap guidewire module 262 may instead include an inserting endpiece (such that it resembles the top endcap guidewire module 260) and each of the plurality of guidewire tips 80, 102, 106, and 84 may instead include a receiving endpiece.

Figure 11D:
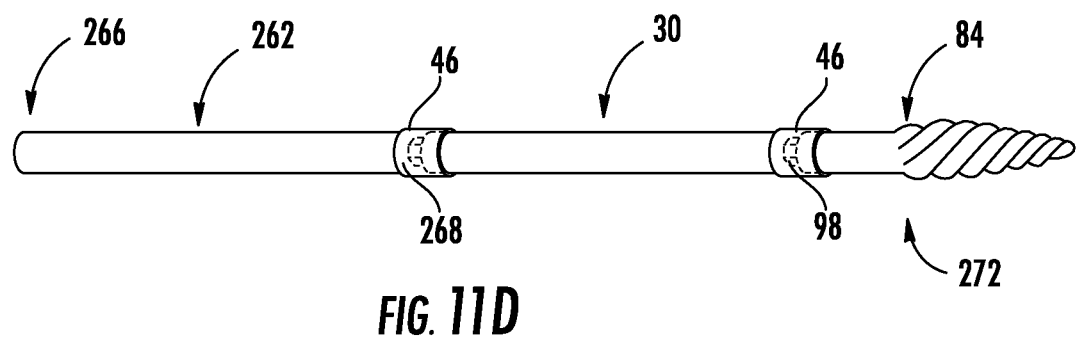
FIG. 11d depicts an embodiment of a modular guidewire including the endcap guidewire module and one of the guidewire tips embodied in FIG. 11c.

FIG. 11d illustrates an embodiment of a modular guidewire, shown as capped and tipped modular guidewire 272. The capped and tipped modular guidewire 272 includes the bottom endcap guidewire module 262 and the screw guidewire tip 84 from FIG. 11c. As shown in FIG. 11d, the non-connecting end 266 of the bottom endcap guidewire module 262 caps one end of the capped and tipped modular guidewire 272, and the screw guidewire tip 84 essentially caps the other end of the modular guidewire 272 (i.e., because no further guidewire modules may be added at the end with the screw guidewire tip 84), such that the capped and tipped modular guidewire 270 does not include exposed connecting endpieces.

As illustrated in FIG. 11d, the screw guidewire tip 84 may be connected to a guidewire modules, such as guidewire module 30, by the inserting endpiece 98. Similarly, the bottom endcap guidewire module 262 may be connected to a guidewire modules, such as guidewire module 30, by the receiving endpiece 268. In the embodiment shown in FIG. 11d, the connections between the screw guidewire tip 84, the bottom endcap guidewire module 262, and the guidewire module 30 are secured with sleeves 46, which aid in preventing rotation and separation at the connections. However, embodiments that do not include sleeves 46, or which include different inserting endpiece and receiving endpiece designs, are also envisioned. Additionally, although not shown in FIG. 11d, the capped and tipped modular guidewire 272 may be assembled such that it includes more than one guidewire module between the selected guidewire tip and the bottom endcap guidewire module 262.

Endcap guidewire modules, such as the top endcap guidewire module 260 and the bottom endcap guidewire module 262, may be provided in a modular guidewire supply kit. A modular guidewire supply kit may include the top endcap guidewire module 260 and/or the bottom endcap guidewire module 262 packaged, individually or together, in sterile trays, sterile containers, etc. as commonly employed for such purposes. The modular guidewire supply kit may also include instructions for use. Furthermore, the modular guidewire supply kit may include unshaped guidewire modules, such as the guidewire module 30 and the graded guidewire modules 72, 74, 76, and 78; shaped guidewire modules, such as the curved guidewire modules 110, 112, 114, and 116 and the undulating guidewire modules 140; and/or a plurality of guidewire tips, such as the guidewire tips shown in FIG. 5a and FIG. 6b. Thus, surgical staff may form a modular guidewire, such as the capped modular guidewire 270 from FIG. 11b or the capped and tipped modular guidewire 272 from FIG. 11d, by selecting the components of the modular guidewire from a modular guidewire supply kit.

Figure 12A:
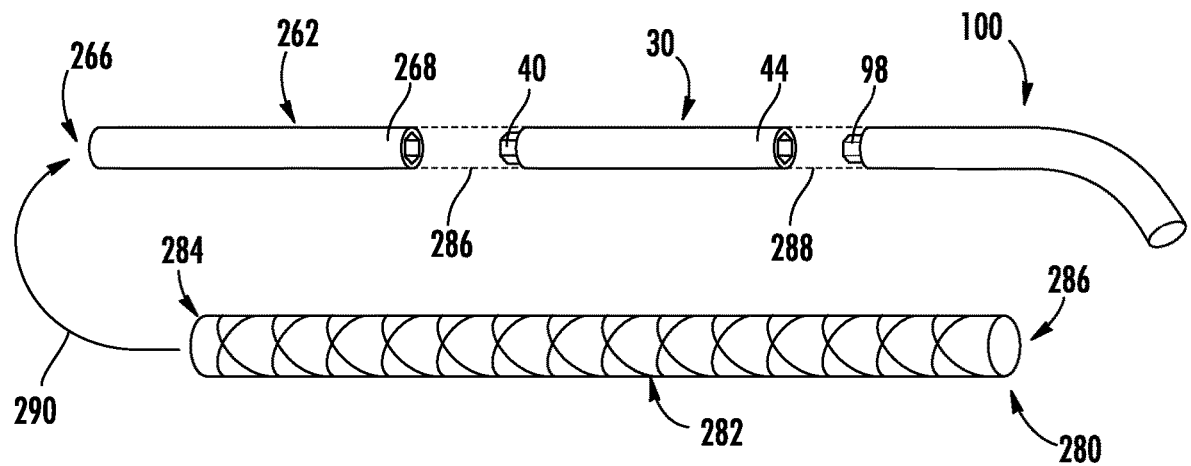
FIG. 12a depicts an embodiment of a disassembled modular guidewire and an embodiment of a guidewire sheath.
Figure 12B:
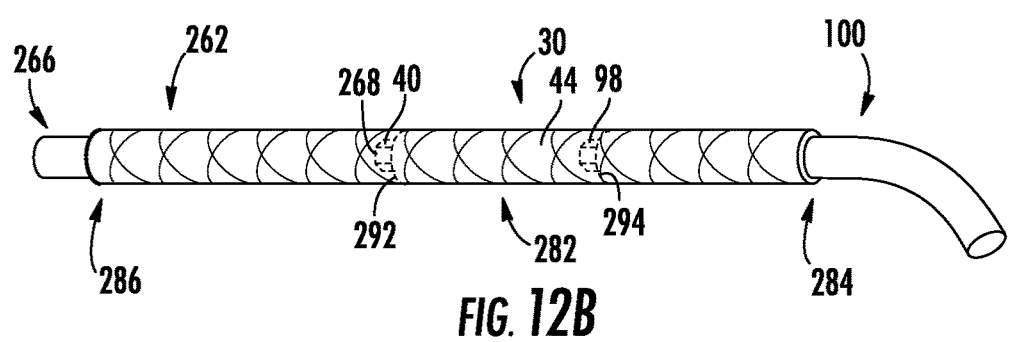

FIGS. 12a and 12b illustrate an embodiment of a modular guidewire, shown as sheathed modular guidewire 280. In the embodiment of FIGS. 12a and 12b, the sheathed modular is formed from a plurality of guidewire modules and a guidewire tip, the guidewire modules and the guidewire tip secured together by a long, cylindrical sheath, shown as sheath 282. FIG. 12a shows example separated components of the sheathed modular guidewire 280: the bottom endcap guidewire module 262, the guidewire module 30, and the slightly bent guidewire tip 100. In the embodiment of FIG. 12a, the bottom endcap guidewire module 262 and the guidewire module 30 are configured to connect together along an insertion path shown by dashed lines 286, i.e., by the receiving endpiece 268 of the bottom endcap guidewire module 262 and the inserting endpiece 40 of the modular guidewire 30. The modular guidewire 30 and the slightly bent guidewire tip 100 are configured to connect together along an insertion path shown by dashed lines 288, i.e., by the receiving endpiece 44 of the modular guidewire 30 and the inserting endpiece 98 of the angled guidewire tip 100. As shown in FIG. 12a, the sheath 282 includes a first end 284 and a second end 286, and is configured to thread over a plurality of connected guidewire modules and/or a plurality of connected guidewire modules further connected to a guidewire tip. In the embodiment of FIG. 12a, the sheath 282 is configured to thread over the bottom endcap guidewire module 262, the guidewire module 30, and the slightly angled guidewire tip 100 once connected together, as shown by arrow 290.

FIG. 12b illustrates the sheathed modular guidewire 280 assembled together. As shown in FIG. 12b, the bottom endcap guidewire module 262, the guidewire module 30, and the slightly bent guidewire tip 100 interlock together via connections 292 (i.e., between the receiving endpiece 268 of the bottom endcap guidewire module 262 and the inserting endpiece 40 of the guidewire module 30) and 294 (i.e., between the receiving endpiece 44 of the guidewire module 30 and the inserting endpiece 98 of the slightly bent guidewire tip 100). The sheath 282 then threads over the connected guidewire modules 262 and the guidewire tip 100, thereby hindering rotation and separation at the connections 292 and 294. In this way, the sheath 282 may serve as an alternative to using sleeves 46 at each connection within a modular guidewire, as shown, e.g., in FIG. 3, FIG. 4, FIG. 11b, and FIG. 11d. The sheath 282 may also be provided as part of a modular guidewire supply kit and be either disposable or reusable.

Figure 13A:
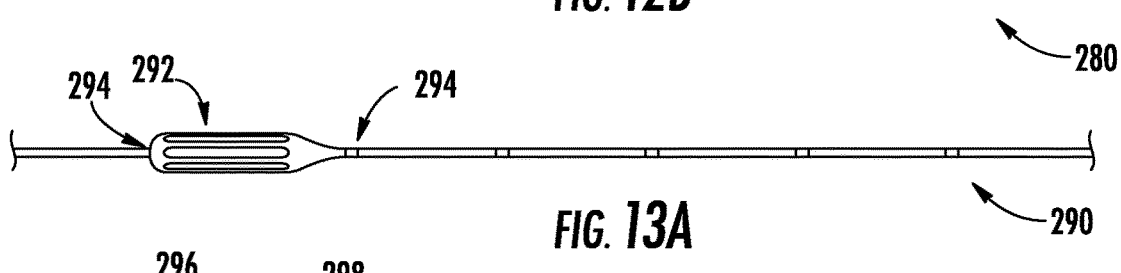
FIG. 13a depicts an embodiment of a modular guidewire threadably attached to an embodiment of a guidewire torque device.
Figure 13B:
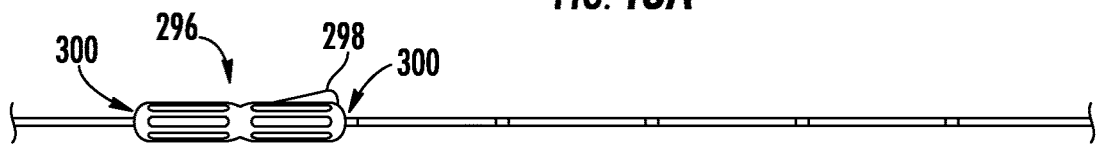
FIG. 13b depicts an embodiment of a modular guidewire threadably attached to a second embodiment of a guidewire torque device.
Figure 13C:
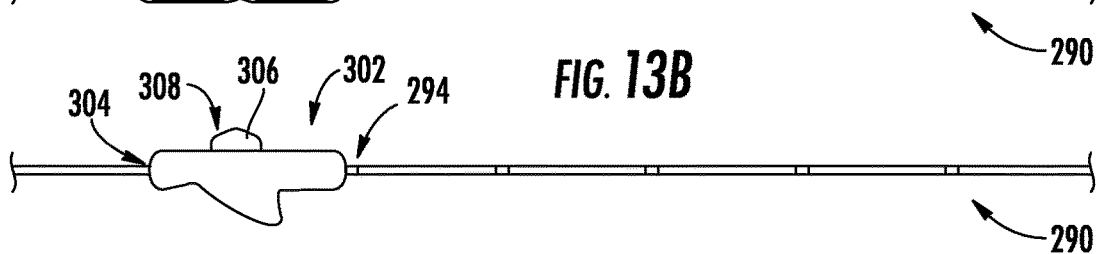
FIG. 13c depicts an embodiment of a modular guidewire threadably attached to a third embodiment of a guidewire torque device.

Once in the body of a patient, a modular guidewire may be manipulated by hand (i.e., a surgeon may manually manipulate the modular guidewire). Alternatively, and as shown in FIGS. 13a-13c, a guidewire torque device may be used to manipulate a modular guidewire within the body of a patient. By way of illustration, a guidewire torque device may be used to advance or retract the modular guidewire within the body, or the guidewire torque device may be used to rotate the modular guidewire in order to guide the modular guidewire into a particular anatomy of the patient. The guidewire torque device may take on a variety of forms; three embodiments of a guidewire torque device are shown in FIGS. 13a-13c. FIG. 13a illustrates a modular guidewire, shown as modular guidewire 290, with a collet torque device 292 attached at one end. The collet torque device 292 may be attached to the modular guidewire 290 by, e.g., threading the modular guidewire 290 through a lumen 294 of the collet torque device 292. Once the collet torque device is attached to the modular guidewire 290, a user may manipulate the modular guidewire 290 by, e.g., pushing or retracting the modular guidewire 290 through the collet torque device 292, or by rotating the collet torque device 292 to thereby rotate the modular guidewire 290.

FIG. 13b shows the modular guidewire 290 with a slide wedge guidewire torque device 296 attached at one end. The slide wedge torque device 296 allows for easy attachment to the modular guidewire 290 by, e.g., squeezing a finger pad 298 of the slide wedge torque device 296, so as to align a lumen 300 of the slide wedge torque device 296 to allow the modular guidewire 290 to thread through the slide wedge torque device 296. To advance or retract the modular guidewire 290 through the slide wedge torque device 296, a user may, e.g., squeeze the finger pad 298 and slide the slide wedge torque device 296 up or down the modular guidewire 290, releasing the finger pad 298 to lock the slide wedge torque device 296 in place on the modular guidewire 290 once the slide wedge torque device 296 is in a desired position on the modular guidewire 290. Once locked, rotating the slide wedge torque device 296 may rotate the modular guidewire 290.

FIG. 13c shows the modular guidewire 290 with a roller wheel torque device 302 attached at one end. The roller wheel torque device 302 may be attached to the modular guidewire 290 by, e.g., threading the modular guidewire 290 into a lumen 304 of the roller wheel torque device 302 and advancing a roller wheel 306 of the roller wheel torque device 302. As the roller wheel 306 is advanced, a scalloped edge 308 of the roller wheel 306 may "grab" onto the modular guidewire 290, thereby advancing the modular guidewire 290 through the lumen 304 of the roller wheel torque device 302. This same process may be used to advance the modular guidewire 290 within the body of a patient by the roller wheel torque device 302, and retraction of the modular guidewire 290 by the roller wheel torque device 302 may be accomplished by spinning the roller wheel 306 in the other direction. As with the collet torque device 292 and the slide wedge torque device 296, rotating the roller wheel torque device 302 may also rotate the modular guidewire 290.

Figure 14:
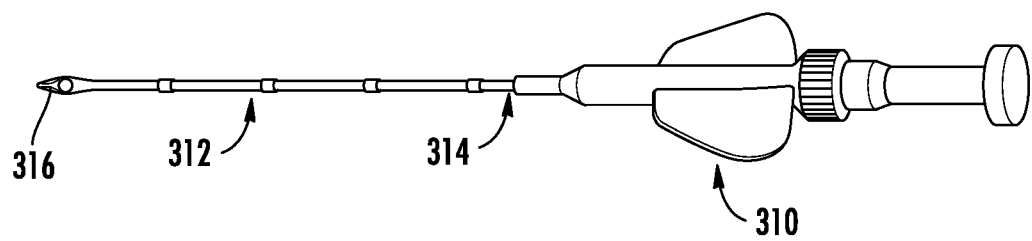
FIG. 14 depicts an embodiment of a modular guidewire connected to a drill attachment.

A modular guidewire may also be advanced into dense portions of a patient's anatomy (e.g., bone) by drilling the guidewire. FIG. 14 illustrates an embodiment of a guidewire drill attachment, shown as drill attachment 310. As shown in FIG. 14, the drill attachment 310 may be attached to a modular guidewire, shown in FIG. 14 as drilling modular guidewire 312, by, e.g., threading the drilling modular guidewire 312 into a lumen 314 of the drill attachment 310.

The, by "turning on" the drill attachment 310, the drill attachment 310 may cause the drilling modular guidewire 312 to drill into the dense anatomy of the patient. Alternatively, the drill attachment 310 may cause the drilling modular guidewire 312 to drill into the dense anatomy due to manual drilling performed by a user (e.g., by the user turning a crank on the drilling attachment 310). In the embodiment of FIG. 14, the drilling modular guidewire 312 includes a threaded trocar tip 316, the sharpness of the threaded trocar tip 316, as well as the threading of the threaded trocar tip 316, may further facilitate the drilling of the drilling modular guidewire 312 into the dense anatomy. However, other guidewire tips and/or modular guidewire designs or configurations may be used in place of the drilling modular guidewire 312 that may also facilitate drilling of the modular guidewire.

Various exemplary embodiments of the invention are described herein. Reference is made to these examples in a non-limiting sense. They are provided to illustrate more broadly applicable aspects of the invention. Various changes may be made to the invention described and equivalents may be substituted without departing from the true spirit, and scope of the invention. In addition, many modifications may be made to adapt a particular situation, material, composition of matter, process, process act(s) or step(s) to the objective(s), spirit or scope of the present invention. Further, as will be appreciated by those with skill in the art, each of the individual variations described and illustrated herein has discrete components and features which may be readily separated from or combined with the features of any of the other several embodiments without departing from the scope or spirit of the present inventions. All such modifications are intended to be within the scope of claims associated with this disclosure.

Any of the guidewire modules, guidewire tips, endcap guidewire modules, etc. may be provided in a kit form. These modular guidewire supply "kits" may further include instructions for use and be packaged in sterile trays or containers as commonly employed for such purposes.

The invention includes methods that may be performed using the subject devices. The methods may include the act of providing such a suitable device. Such provision may be performed by the end user. In other words, the "providing" act merely requires the end user obtain, access, approach, position, set-up, activate, power-up, or otherwise act to provide the requisite device in the subject method. Methods recited herein may be carried out in any order of the recited events that is logically possible, as well as in the recited order of events.

Exemplary aspects of the invention have been set forth above. As for other details of the present invention, these may be appreciated in connection with patents and publications generally known or appreciated by those with skill in the art. The same may hold true with respect to method-based aspects of the invention in terms of additional acts as commonly or logically employed by those with skill in the art.

In addition, though the invention has been described in reference to several examples optionally incorporating various features, the invention is not to be limited to that which is described or indicated as contemplated with respect to each variation of the invention. Various changes may be made to the invention described and equivalents (whether recited herein or not included for the sake of some brevity) may be substituted without departing from the true spirit and scope of the invention. In addition, where a range of values is provided, it is understood that every intervening value, between the upper and lower limit of that range and any other stated or intervening value in that stated range, is encompassed within the invention.

Also, it is contemplated that any optional feature of the inventive variations described may be set forth and claimed independently, or in combination with any one or more of the features described herein. Reference to a singular item, includes the possibility that there are plural of the same items present. More specifically, as used herein and in claims associated hereto, the singular forms "a," "an," "said," and "the" include plural referents unless specifically stated otherwise. In other words, use of the articles allow for "at least one" of the subject item in the description above as well as claims associated with this disclosure. It is further noted that such claims may be drafted to exclude any optional element. As such, this statement is intended to serve as antecedent basis for use of such exclusive terminology as "solely," "only" and the like in connection with the recitation of claim elements, or use of a "negative" limitation.

Without the use of such exclusive terminology, the term "comprising" in claims associated with this disclosure shall allow for the inclusion of any additional element—irrespective of whether a given number of elements are enumerated in such claims or the addition of a feature could be regarded as transforming the nature of an element set forth in such claims. Except as specifically defined herein, all technical and scientific terms used herein are to be given as broad a commonly understood meaning as possible while maintaining claim validity.

The breadth of the present invention is not to be limited to the examples provided and/or the subject specification, but rather only by the scope of claim language associated with this disclosure.

What is claimed is:

1. A guidewire having a first end and a second end, the guidewire comprising:
    two or more guidewire modules,
    wherein each guidewire module has an inserting endpiece at a first end and a receiving endpiece at a second end, the inserting endpiece comprising a solid hexagonal shaped prism and extending from a body of the guidewire module and the receiving endpiece comprising a recess having a floor with a hexagonal shape and six sidewall portions coordinating with the solid hexagonal shaped prism of the inserting endpiece;
    wherein a first guidewire module is configured to be attachable to a second guidewire module by inserting the inserting endpiece of the first guidewire module into the receiving endpiece of the second guidewire module; and
    wherein the inserting endpiece and the receiving endpiece are configured to prevent rotation and allow longitudinal movement between the first guidewire module and second guidewire module when the inserting endpiece is received by the receiving endpiece.

2. The guidewire of claim 1, the guidewire further comprising a guidewire tip attached at the first end or the second end of the guidewire.

3. The guidewire of claim 2, wherein the guidewire tip is removably attached at the first or the second end of the guidewire.

4. The guidewire of claim 3, wherein the guidewire tip is selected from a guidewire tip set comprising at least two of a straight guidewire tip, a ball guidewire tip, a bent guidewire tip, a J-curved guidewire tip, a screw guidewire tip, a hooked guidewire tip, a trocar guidewire tip, a drill guidewire tip, a magnetic guidewire tip, and an adhesive guidewire tip.

5. The guidewire of claim 1, the guidewire further comprising a plurality of sleeves configured to threadably cover the inserting and receiving endpieces when connected.

6. The guidewire of claim 1, wherein the guidewire is configured to be used through manual manipulation by a user.

7. The guidewire of claim 1, wherein the guidewire is configured to be used with a drill attachment.

8. The guidewire of claim 1, wherein the two or more guidewire modules are configured to be rigidly locked together for advancement into bone tissue.

9. A modular guidewire supply kit, comprising:
three or more guidewire modules, each guidewire module having an inserting endpiece at a first end and a receiving endpiece at a second end, the inserting endpiece comprising a solid hexagonal shaped prism and extending from a body of the guidewire module and the receiving endpiece comprising a recess having a floor with a hexagonal shape and six sidewall portions coordinating with the solid hexagonal shaped prism of the inserting endpiece;
wherein a first guidewire module is configured to be attachable to a second guidewire module by inserting the inserting endpiece of the first guidewire module into the receiving endpiece of the second guidewire module; and
wherein the inserting endpiece and the receiving endpiece are configured to prevent rotation and allow longitudinal movement between the first guidewire module and second guidewire module when the inserting endpiece is received by the receiving endpiece,
wherein a completed guidewire comprises at least two of the three or more guidewire modules attached together.

10. The modular guidewire supply kit of claim 9, the modular guidewire kit further comprising one or more guidewire tips configured to be attachable to at least the first end or the second end of at least one of the three or more guidewire modules, and wherein the completed guidewire further comprises a guidewire tip of the one or more guidewire tips attached to one of the two or more modules attached together.

11. The modular guidewire supply kit of claim 10, wherein the one or more guidewire tips are comprised of one of a straight guidewire tip, a ball guidewire tip, a bent guidewire tip, a J curved guidewire tip, a screw guidewire tip, a hooked guidewire tip, a trocar guidewire tip, a drill guidewire tip, a magnetic guidewire tip, and an adhesive guidewire tip.

12. The modular guidewire supply kit of claim 9, further comprising a plurality of sleeves configured to threadably cover the inserting and receiving endpieces when connected.

13. A method for building a guidewire of customizable length, the method comprising:
determining a desired length for a guidewire;
selecting at least two guidewire modules from a set comprising at least three guidewire modules, each guidewire module having an inserting endpiece at a first end and a receiving endpiece at a second end, the inserting endpiece comprising a solid hexagonal shaped prism and extending from a body of the guidewire module and the receiving endpiece comprising a recess having a floor with a hexagonal shape and six sidewall portions coordinating with the solid hexagonal shaped prism of the inserting endpiece;
attaching the two or more guidewire modules together by inserting the inserting endpiece of a first guidewire module into the receiving endpiece of a second guidewire module, such that when the inserting endpiece is received by the receiving endpiece the inserting endpiece and the receiving endpiece prevent rotation and allow longitudinal movement between the first guidewire module and second guidewire module; and
attaching a guidewire tip to the first end or the second end of one of the attached two or more guidewire modules, the guidewire of customizable length comprising the attached two or more guidewire modules and the guidewire tip.

14. The method for building the guidewire of customizable length of claim 13, the method further comprising selecting the guidewire tip from a guidewire tip set comprising at least two of a straight guidewire tip, a ball guidewire tip, a bent guidewire tip, a J-curved guidewire tip, a screw guidewire tip, a hooked guidewire tip, a trocar guidewire tip, a drill guidewire tip, a magnetic guidewire tip, and an adhesive guidewire tip.

15. The method for building the guidewire of customizable length of claim 13, the method further comprising sliding a sleeve over each of the inserting and receiving endpieces when connected, the sleeve configured to threadably cover the inserting and receiving endpieces.

16. The method for building the guidewire of customizable length of claim 13, the method further comprising:
inserting the guidewire of customizable length into a body of a patient; and
manipulating the guidewire within an anatomy of the patient.

17. The method for building the guidewire of customizable length of claim 16, wherein the manipulating the guidewire within the anatomy of the patient comprises manipulating the guidewire by at least one of manual manipulation, using a guidewire torque device, or using a drill attachment coupled to the end of the guidewire.

18. The method for building the guidewire of customizable length of claim 13, further comprising removing, from the guidewire of customizable length, a guidewire module determined to be fatigued or unsuitable for use and replacing the removed guidewire module with a new guidewire module from the set comprising at least three guidewire modules.

* * * * *